(12) United States Patent
Wang

(10) Patent No.: US 10,379,048 B2
(45) Date of Patent: Aug. 13, 2019

(54) FLUORESCENCE BIOPSY SPECIMEN IMAGER AND METHODS

(71) Applicant: LI-COR, Inc., Lincoln, NE (US)

(72) Inventor: Han-Wei Wang, Lincoln, NE (US)

(73) Assignee: LI-COR, INC., Lincoln, NE (US)

( * ) Notice: Subject to any disclaimer, the term of this patent is extended or adjusted under 35 U.S.C. 154(b) by 223 days.

(21) Appl. No.: 15/192,771

(22) Filed: Jun. 24, 2016

(65) Prior Publication Data
US 2016/0377545 A1 Dec. 29, 2016

Related U.S. Application Data

(60) Provisional application No. 62/339,657, filed on May 20, 2016, provisional application No. 62/325,588, (Continued)

(51) Int. Cl.
*G01N 21/64* (2006.01)
*G06F 3/0484* (2013.01)
(Continued)

(52) U.S. Cl.
CPC ..... *G01N 21/6456* (2013.01); *G01N 21/6458* (2013.01); *G01N 21/6486* (2013.01);
(Continued)

(58) Field of Classification Search
CPC .......... G01N 21/6456; G01N 21/6486; G01N 21/6458
See application file for complete search history.

(56) References Cited

U.S. PATENT DOCUMENTS

| 2,792,502 A | 5/1957 | O'Connor et al. |
| 5,103,338 A | 4/1992 | Crowley et al. |

(Continued)

FOREIGN PATENT DOCUMENTS

| CN | 101301192 | 11/2008 |
| CN | 102048525 | 5/2012 |

(Continued)

OTHER PUBLICATIONS

"Arctec Eva Fast Handheld 3D Scanner for Professionals," http://www.artec3d.com/hardware/artec-evat/, retrieved Apr. 19, 2016, 6 pages.
(Continued)

*Primary Examiner* — Yara B Green
(74) *Attorney, Agent, or Firm* — Kilpatrick Townsend & Stockton LLP

(57) ABSTRACT

An imaging device is described that uses multiple cameras to image a biological sample on a turntable bathed in white light or fluorescing due to a systemically administered dye. Fluorescence farther away from an excitation light source can be compensated upon determining a 3-D position of portions of the sample. The turntable is turned and tilted in order to take enough images to prepare an animation of the sample. In a graphical user interface, the animation can be stopped, zoomed, and tilted per a user's gesture, touch, tablet-tilting, or other commands. The image manipulation can be with touch gestures entered using a sterilizable or disposable touch pen.

16 Claims, 39 Drawing Sheets

Related U.S. Application Data filed on Apr. 21, 2016, provisional application No. 62/185,407, filed on Jun. 26, 2015.

(51) Int. Cl.

| | | |
|---|---|---|
| *G06F 3/0485* | (2013.01) | |
| *G06F 3/0488* | (2013.01) | |
| *H04N 5/225* | (2006.01) | |
| *G06T 7/55* | (2017.01) | |
| *G02B 21/16* | (2006.01) | |
| *G02B 27/22* | (2018.01) | |
| *G06F 3/0354* | (2013.01) | |
| *G01N 21/17* | (2006.01) | |

(52) U.S. Cl.
CPC ......... *G02B 21/16* (2013.01); *G02B 27/2271* (2013.01); *G06F 3/0485* (2013.01); *G06F 3/04845* (2013.01); *G06F 3/04847* (2013.01); *G06F 3/04886* (2013.01); *G06T 7/55* (2017.01); *H04N 5/2251* (2013.01); *H04N 5/2256* (2013.01); *G01N 2021/1776* (2013.01); *G06F 3/03545* (2013.01); *G06T 2207/10064* (2013.01); *G06T 2207/30096* (2013.01); *G06T 2207/30204* (2013.01)

(56) References Cited

U.S. PATENT DOCUMENTS

| | | | |
|---|---|---|---|
| 5,224,141 A | | 6/1993 | Yassa et al. |
| 5,408,294 A | * | 4/1995 | Lam ................. G03B 35/14 348/87 |
| 5,812,265 A | | 9/1998 | Hoshiyama |
| 5,959,295 A | * | 9/1999 | Braun ............... G01D 5/2457 250/231.16 |
| 6,165,170 A | | 12/2000 | Wynne et al. |
| 6,356,272 B1 | | 3/2002 | Matsumoto et al. |
| RE37,913 E | | 11/2002 | Nishi |
| 6,711,433 B1 | | 3/2004 | Geiger et al. |
| 7,218,393 B2 | | 5/2007 | Sharpe et al. |
| 7,286,232 B2 | | 10/2007 | Bouzid |
| 7,453,456 B2 | | 11/2008 | Petrov et al. |
| 7,505,124 B2 | | 3/2009 | Kreckel et al. |
| 7,551,711 B2 | | 6/2009 | Sarment et al. |
| 7,715,523 B2 | | 5/2010 | Lafferty |
| 7,929,743 B2 | | 4/2011 | Khorasani |
| 8,115,918 B2 | | 2/2012 | Zavislan et al. |
| 8,220,415 B2 | | 7/2012 | Ragatz et al. |
| 8,503,602 B2 | | 8/2013 | Lafferty |
| 8,741,232 B2 | | 6/2014 | Baysal et al. |
| 8,754,384 B1 | | 6/2014 | Persoon et al. |
| 8,851,017 B2 | | 10/2014 | Ragatz et al. |
| 8,892,192 B2 | | 11/2014 | Cuccia et al. |
| 9,053,563 B2 | | 6/2015 | Embrey |
| 9,557,281 B2 | | 1/2017 | Yang et al. |
| 9,632,187 B2 | | 4/2017 | Poon et al. |
| 2003/0078477 A1 | * | 4/2003 | Kang .................. A61B 1/042 600/178 |
| 2004/0101088 A1 | | 5/2004 | Sabol et al. |
| 2005/0046840 A1 | | 3/2005 | Kusuzawa |
| 2005/0227374 A1 | | 10/2005 | Cunningham |
| 2006/0072123 A1 | * | 4/2006 | Wilson ............... G01B 11/2518 356/609 |
| 2006/0250518 A1 | | 11/2006 | Nilson et al. |
| 2006/0253035 A1 | | 11/2006 | Stern |
| 2007/0121099 A1 | * | 5/2007 | Matsumoto ........ G01N 21/6428 356/72 |
| 2007/0276184 A1 | | 11/2007 | Okawa |
| 2008/0077019 A1 | | 3/2008 | Xiao et al. |
| 2008/0312540 A1 | | 12/2008 | Ntziachristos |
| 2009/0011386 A1 | | 1/2009 | Eiff et al. |
| 2009/0018451 A1 | | 1/2009 | Bai et al. |
| 2009/0032731 A1 | | 2/2009 | Kimura et al. |
| 2009/0129543 A1 | | 5/2009 | Le Gros et al. |
| 2009/0192358 A1 | | 7/2009 | Jaffer et al. |
| 2009/0208072 A1 | | 8/2009 | Seibel et al. |
| 2009/0234225 A1 | | 9/2009 | Martin et al. |
| 2009/0250631 A1 | | 10/2009 | Feke et al. |
| 2010/0309548 A1 | | 12/2010 | Power et al. |
| 2011/0116694 A1 | | 5/2011 | Gareau |
| 2011/0135190 A1 | | 6/2011 | Maad |
| 2011/0229023 A1 | | 9/2011 | Jones et al. |
| 2012/0049088 A1 | | 3/2012 | Klose |
| 2012/0065518 A1 | | 3/2012 | Mangoubi et al. |
| 2012/0105600 A1 | * | 5/2012 | Meyer ................ G01N 21/49 348/50 |
| 2012/0194663 A1 | | 8/2012 | Haisch et al. |
| 2012/0200577 A1 | | 8/2012 | Guckenberger et al. |
| 2012/0302880 A1 | | 11/2012 | Tian et al. |
| 2012/0312957 A1 | | 12/2012 | Loney et al. |
| 2013/0027516 A1 | | 1/2013 | Hart et al. |
| 2013/0135081 A1 | | 5/2013 | Mccloskey et al. |
| 2014/0125790 A1 | | 5/2014 | Mackie et al. |
| 2014/0140594 A1 | | 5/2014 | Mahadevan-Jansen et al. |
| 2014/0163388 A1 | | 6/2014 | Sasayama et al. |
| 2014/0276008 A1 | | 9/2014 | Steinbach et al. |
| 2014/0294247 A1 | | 10/2014 | Sirault et al. |
| 2014/0346359 A1 | | 11/2014 | Holliday |
| 2014/0349337 A1 | * | 11/2014 | Dasari ................ G01N 33/49 435/40.5 |
| 2014/0378843 A1 | | 12/2014 | Valdes et al. |
| 2015/0000410 A1 | | 1/2015 | Grimard et al. |
| 2015/0022824 A1 | | 1/2015 | Babayoff |
| 2015/0062153 A1 | | 3/2015 | Mihalca et al. |
| 2015/0073213 A1 | | 3/2015 | Khait et al. |
| 2015/0098126 A1 | | 4/2015 | Keller et al. |
| 2015/0105283 A1 | | 4/2015 | Weiss et al. |
| 2015/0359413 A1 | | 12/2015 | Rainis |
| 2016/0187199 A1 | | 6/2016 | Brunk et al. |
| 2017/0059487 A1 | | 3/2017 | Wang |
| 2017/0309063 A1 | | 10/2017 | Wang |
| 2017/0336706 A1 | | 11/2017 | Wang |
| 2017/0367582 A1 | | 12/2017 | Wang |
| 2018/0140197 A1 | | 5/2018 | Wang et al. |

FOREIGN PATENT DOCUMENTS

| | | |
|---|---|---|
| CN | 103082997 | 10/2015 |
| DE | 10 2011 104 216 A1 | 12/2012 |
| GB | 2514125 | 11/2014 |
| KR | 20130096910 | 9/2013 |
| WO | 2006113908 | 10/2006 |
| WO | 2007/030424 A2 | 3/2007 |
| WO | 2009/115061 A1 | 9/2009 |
| WO | 2013166497 | 11/2013 |
| WO | 2016014252 | 1/2016 |
| WO | 2016073569 | 5/2016 |
| WO | 2016/100214 A1 | 6/2016 |
| WO | 2016210340 | 12/2016 |
| WO | 2017184940 | 10/2017 |
| WO | 2017200801 | 11/2017 |
| WO | 2017223378 | 12/2017 |
| WO | 2018098162 A1 | 5/2018 |

OTHER PUBLICATIONS

"BioVision Digital Specimen Radiography (DSR) System," (Bioptics, Inc.), Premarket Notification 510(k) Summary, May 2009, 5 pages.

Fang et al., "Combined Optical and X-ray Tomosynthesis Breast Imaging," Radiology, Jan. 2011, vol. 258, No. 1, pp. 89-97.

FAXITRON—"BioVision Surgical Specimen Radiography System," Faxitron Bioptics LLC, http://www.faxitron.com/medical/products/biovision.html, Retrieved Apr. 18, 2016, 2 pages.

FAXITRON—"Path Vision," Faxitron Bioptics LLC, http://www.faxitron.com/medical/products/pathvision.html, Retrieved Apr. 18, 2016, 2 pages.

International Application No. PCT/US2016/018972, International Search Report and Written Opinion dated Jun. 23, 2016, 10 pages.

International Application No. PCT/US2016/039382, International Search Report and Written Opinion dated Sep. 13, 2016, 14 pages.

(56) References Cited

OTHER PUBLICATIONS

"Optical Scatter Imaging System for Surgical Specimen Margin Assessment During Breast Conserving Surgery," Project Information, U.S. Department of Health & Human Services, NIH Research Portfolio Online Reporting Tools, Updated Apr. 18, 2016, Project No. 1RO1CA192803-01, https://projectreporter.nih.gov/project_info_description.cfm?aid=8840807&icde=2828016& . . . , 2 pages.
PerkinElmer, "Every Cancer Tells a Story if You Have the Tools to Read It," Solutions for Cancer Research, AACR Annual Meeting, Apr. 18-22, 2015, http://go.perkinelmer.com/webmail/32222/179460051/9c4865b118d5295e96e973a5b6c28bad, 2 pages.
PerkinElmer, "Every Cancer Tells a Story if You Have the Tools to Read It," http://go.perkinelmer.com/1/32222/2015-03-26/3rww9?utm_content=LST-AACR-GLO-Q . . . Retrieved Apr. 15, 2015, 2 pages.
TomoWave Laboratories "Imaging Modules," http://www.tomowave.com/imaging-modules.html, Retrieved Apr. 18, 2016, 1 page.
Wu et al. "Rotational imaging optical coherence tomography for full-body mouse embryonic imaging," *Journal of Biomedical Optics*, Feb. 2016, vol. 21(2), pp. 026002-1-026002-9.
International Search Report dated Feb. 8, 2018, for PCT Appln No. PCT/US2017/062812, 3 pages.
Lamberts et al., "Tumor-specific uptake of fluorescent bevacizumab-IRDye800CW microdosing in patients with primary breast cancer: a phase I feasibility study", Clinical Cancer Research, Personalized Medicine and Imaging, American Association for Cancer Research, Nov. 9, 2016, 41 pages.
Lee et al., "Fusion of coregistered cross-modality images using a temporally alternating display method", Medical & Biological Engineering & Computing, Springer, vol. 38, No. 2, Mar. 1, 2000, pp. 127-132.
International Search Report and Written Opinion dated Sep. 22, 2017 for PCT/US2017/028769, 19 pages.
International Search Report and Written Opinion dated Sep. 19, 2017 for PCT/US2017/031740, 25 pages.
International Search Report and Written Opinion dated Sep. 22, 2017 for PCT/US2017/038860, 13 pages.
U.S. Appl. No. 15/352,427, "Notice of Allowance," dated Nov. 21, 2018, 6 pages (not attached).
EP16756129.9, "Partial European Search Report," dated Oct. 29, 2018, 17 pages.
Badawi et al., Real-Time Tissue Assessment During Surgical Procedures, UC David Office of Research, Tech ID: 24307.
Orpheus Medical, Clinical Video Management and Visible Light Documentation, Slideshow dated Feb. 3, 2016. The Examiner's attention is directed to slide 11.
U.S. Appl. No. 15/352,427, "Non-Final Office Action", dated Sep. 4, 2018, 9 pages (available on PAIR).
PCT/US2018/027978 , "International Search Report and Written Opinion", dated Jul. 12, 2018, 13 pages.
Sturm et al., "CopyMe3D: Scanning and Printing Persons in 3D", Medical Image Computing and Computer-Assisted Intervention—Miccai 2015: 18th International Conference, Munich, Germany, Sep. 3-6, 2013, pp. 405-414.

\* cited by examiner

FLUORESCENCE BIOPSY SPECIMEN IMAGER AND METHODS

CROSS-REFERENCES TO RELATED APPLICATIONS

This application claims the benefit of priority to U.S. patent application Ser. No. 62/185,407, filed Jun. 26, 2015, and Ser. No. 62/325,588, filed Apr. 21, 2016, and Ser. No. 62/339,657, filed May 20, 2016, all of which are incorporated by reference in their entireties for all purposes.

STATEMENT AS TO RIGHTS TO INVENTIONS MADE UNDER FEDERALLY SPONSORED RESEARCH AND DEVELOPMENT

Not Applicable

BACKGROUND

A primary purpose of cancer surgery and surgical pathology is to remove tumor tissues. Complete removal of tumors and all tumor tissue is important. If a tumor is not completely removed, then a second surgery may be required. This produces unneeded patient anxiety and risk, delays the start of second stage therapies, and incurs additional financial costs.

In order to completely remove all tumor tissue, surgeons and pathologists work together during surgery to assess tumor margins such that no malignant cells remain in the wound bed. Tumor margins are the healthy tissue surrounding the tumor, more specifically, the distance between the tumor tissue and the edge of the surrounding tissue removed along with the tumor. Ideally, the margins are selected so that the risk of leaving tumor tissue within the patient is low.

Intraoperative pathology consultation guides the cancer surgeon during surgery to assess if the tumor and margin have not been completely excised. Current surgical pathology consultation relies on palpation, visualization, and anatomical features to select sampling areas for frozen section analysis, which is often limited to 20-30 minutes. Intraoperative pathology consultation starts with gross examination of the excised tissues to choose areas for sampling. This is followed by dissection, embedding, frozen sectioning, and staining of 5-μm slice sections of the excised tissue.

The limited surgical consultation timeframe allows only a small portion of the resected tissue to be interpreted by the pathologist. This time crunch can result in sampling errors which negatively impact the patient outcome.

There exists a need in the art for better intraoperative tumor tissue analysis.

BRIEF SUMMARY

Generally disclosed is a device that provides a nearly full, 360° rotation plus limited elevation-angle, three-dimensional (3D) images of a tumor sample that has been systemically labeled using a fluorescence dye. A first camera takes full-color pictures of the tumor sample at different azimuth and elevation angles; a second camera captures fluorescence images of the sample at the same angles while the sample is illuminated at an excitation frequency. Because of the low light levels of fluorescence, sensitivity-improving approaches, such as active cooling, imaging with a monochrome sensor, long exposure durations, and electronic noise suppression methods, can be used with the second camera.

The resulting full-color and fluorescence images are either overlaid or used to make 3D computer models that are overlaid in space. For making 3D models, calibration marks on a window platform help the software generate precise 3D grids and sub-volumes in order to determine the position of each surface in the images.

The imager can generate a full rotation 3D image of a sample and present it in interactive animation as well as in an augmented realty 3D model to help localize diseased regions around the whole surgical sample.

A graphical user interface (GUI) aids a surgeon by presenting the images in a filmstrip manner on a touch screen device. A surgeon can swipe the filmstrip left or right in order to rotate views in azimuth around the sample. By swiping up or down, the surgeon can access views of the sample taken from higher or lower in elevation.

Also provided is a touch pen comprising a pen body and a pen tip. The pen tip is attached to an end of the pen body. The touch pen is sterile and does not dispense ink. In some embodiments, the pen body comprises stainless steel. In some embodiments, the pen tip is detachable from the pen body and replaceable with a second pen tip. In some embodiments, the touch pen further comprises a pen cover. The pen cover encloses the pen body and the pen tip, and is sterile.

Due to divergence, excitation light excites fluorescence less at farther points on the sample. This can be corrected for by determining the distance of each surface from the fluorescence excitation light source and adjusting the resulting reading's intensity.

The device will help localize disease tissues to reduce sampling errors and re-examination, and ultimately reduce local cancer recurrence and second surgery costs. The device can be used for image-guided pathology to screen resected tissue or biopsy triage in conjunction with image-guide surgery.

DETAILED DESCRIPTION

Intraoperative consultations are among the most stressful parts of a pathologist's duties. With a strict time limit, little or no ancillary studies available, and using only touch and visual cues to select a few tissue sections to analyze, the pathologist must make a diagnosis where clinical consequences are quite significant.

Imaging modalities currently used in patient care include magnetic resonance imaging (MRI), ultrasound, radiography (X-ray), single-photon emission computed tomography (SPECT), and positron emission tomography (PET). These imaging techniques are not generally used to localize disease in tissues for margin determinations. The reason for this is in part that the resolution offered by these five imaging technologies is not sufficient. Further, the non-specific contrast agents typically used by MRI, ultrasound, and X-ray computed tomography do not target tumors. Additionally, the use of radioactive isotopes in SPECT and PET imaging introduces safety and wellness concerns and is financially costly for both patients and care providers.

An alternative pseudo tomography imaging system embodiment can be used to satisfy the critical criteria for clinical utility. The proposed technology can provide the speed and throughput, the resolution, and the sensitivity and specificity needed to offer a solution for enhancing intraoperative pathology consultation. The described embodiments can also be used within the current work flow of surgeries without significant alterations.

An imaging device as described herein can relieve the diagnosis stress while helping to visualize and identify suspicious areas in lesion samples. It is foreseeable that the device will be used to assist intraoperative consultation of primary tumors and biopsies of head and neck cancers, lymph nodes, hepatobiliary, breast, female genital tract, skin tumors, etc. The proposed technology would also provide cost savings to the healthcare system by reducing reoperations due to recurrence. It is notable that this invention can provide a new paradigm in cancer surgery without causing a deviation from current work flow.

Figure 1:
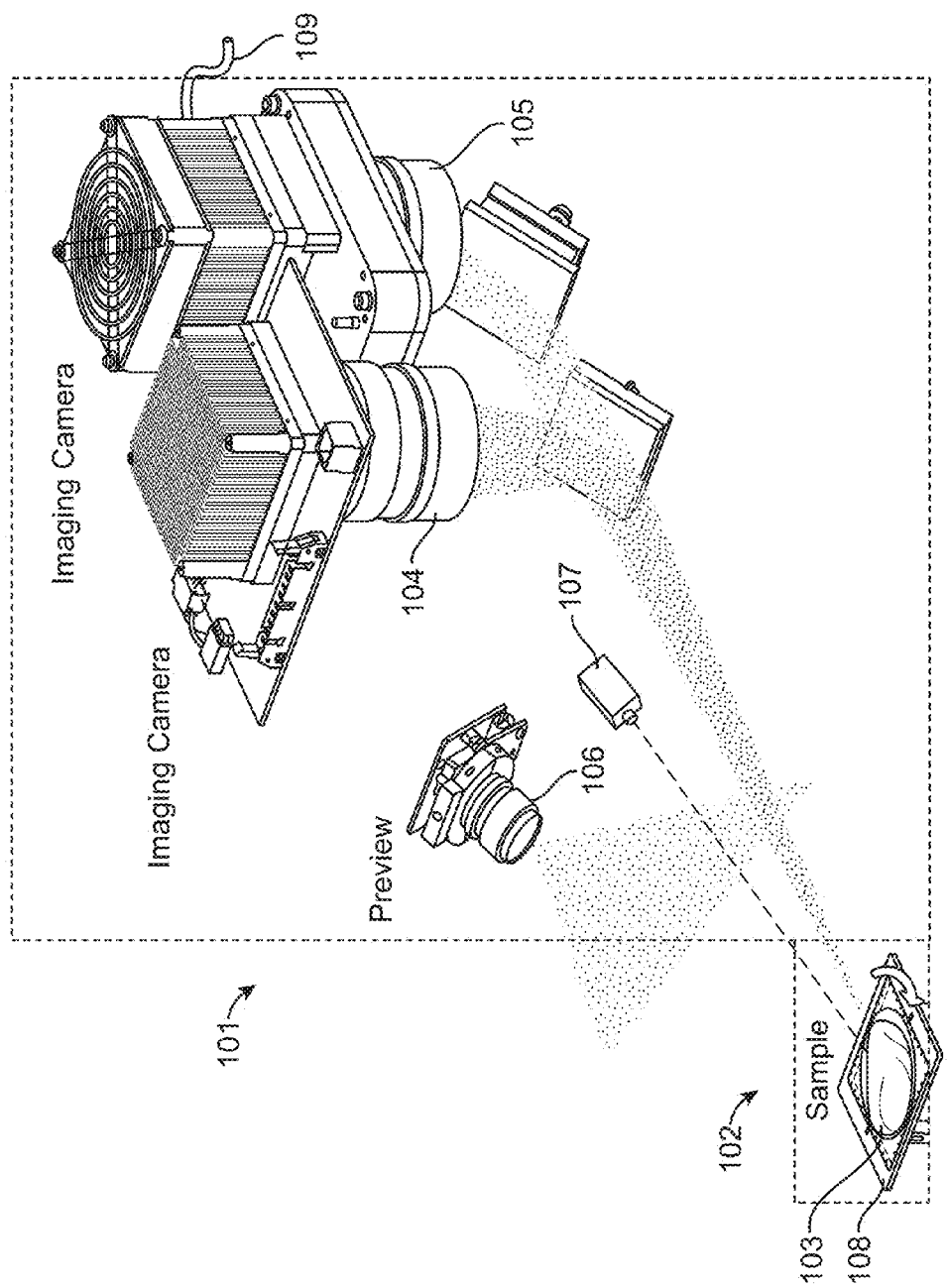
FIG. 1 illustrates a multiple-camera imaging system in accordance with an embodiment.

FIG. 1 illustrates a multiple-camera imaging system in accordance with an embodiment. The imaging system comprises an optical engine 101 for excitation and signal collection; a pseudo-tomography platform 102 comprising a rotatable stage 108 for positioning and rotation of a sample 103; and software (not shown) for operation, imaging, and generation of 3D results. The optical engine 101 comprises a first imaging camera 104 and a second imaging camera 105. Typically the first 104 and second 105 imaging cameras record information using two different imagining modalities. For example, one of the two cameras can be a color camera used for reflected light imaging. The other camera can be a monochromatic camera for fluorescence signal collection. A monochromatic camera includes an imaging device having a sensitivity to a particular wavelength or range of wavelengths while having an insensitivity to a second range of wavelengths, or as otherwise known in the art.

The optical engine 101 can also comprise a preview camera 106. The preview camera 106 can be a true-color zoom camera module used to take preview images and videos in real-time at user-selected view angles.

A laser system 107 can be positioned and configured to illuminate sample 103 with an excitation wavelength. In some embodiments, the excitation wavelength is within the second range of wavelengths that the monochromatic camera is insensitive to.

All three of the cameras 104, 105, and 106 can be configured to have a depth of focus that coincides with the location of the sample 103 on the pseudo-tomography platform 102. The illumination light fields and fields-of view of the cameras 104, 105, and 106, can further be configured along with the depths of focus to provides an imaging resolution of 100 line pairs per inch.

The optical engine 101 can also comprise a cooling line 109. The cooling line 109 can be used provide liquid or other coolant to camera 105 in order to maintain a preferred camera temperature and increase camera sensitivity.

The tomography platform 102 allows nearly full-rotation sample scanning and positioning for tomography imaging and sample loading. This is accomplished through tilting and rotation of the sample stage 107 holding the sample 103. Tilting of the sample stage 107 allows projection views of the top and bottom of the sample 103.

In some embodiments, and as shown in FIG. 1, the system comprises two imaging cameras as well as a preview camera. The preview camera can be used for taking a 'preview' picture of the entire sample for annotation of a respective data file storing image information. The preview pictures can also be used to determine if the sample is properly within the imaging volume. An embodiment can include a full-color camera to provide a sample preview (at, for example, 1280×720 pixels, 15 frame/second, >4-inch field of view) and an isometric picture of a sample for documentary requirement before beginning the 3D tomographic imaging. A software application can be used for a real-time preview function.

In some embodiments, a first imaging camera is used for collecting an image over a broad spectrum of visible wavelengths. In some embodiments, the first camera is a grayscale camera. In some embodiments, the first camera is a full color camera.

In some embodiments, the second imaging camera is a cooled camera configured to capture fluorescence images at very low light levels. In some embodiments, a cooling fan, liquid cooling elements, and other cooling systems can be used to cool the second imaging camera. The camera can be optimized for collecting near infrared wavelength photons.

The imaging cameras are configured to take pictures of the sample from the same orientation and at the same focal depth as one another. There are several different ways to achieve this.

Figure 2:
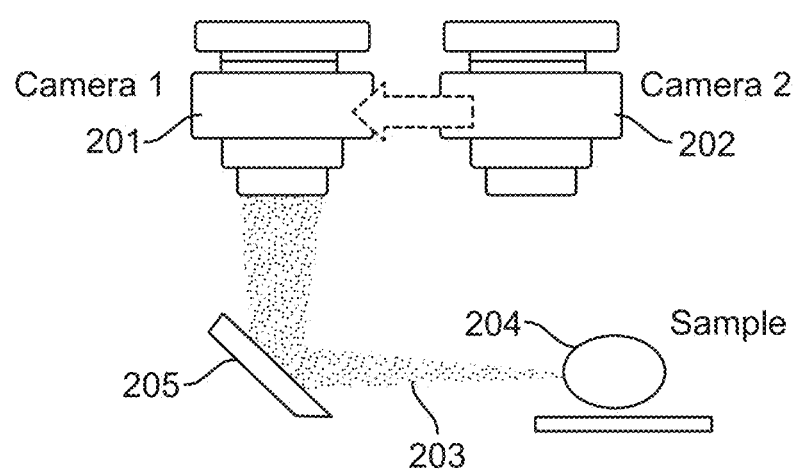
FIG. 2 illustrates a switchable camera configuration in accordance with an embodiment.

FIG. 2 illustrates a switchable camera configuration in accordance with an embodiment. The first 201 and second 202 imaging cameras can be rotated or translated into a position such that their optics focus at the same depth within the imaging volume. This can be accomplished by alternately positioning the first 201 and second 202 cameras such that one of these cameras at a time is positioned to receive light 203 reflecting or emitting from the sample 204 and reflecting off of a mirror 205. In some embodiments, a pivot location offset from the first 201 and second 202 cameras is used to rotate the cameras. In some embodiments, a slide with detents is used to translate the first 201 and second 202 cameras, The slide can be made from metal, plastic, or other suitable rigid materials.

Figure 3:
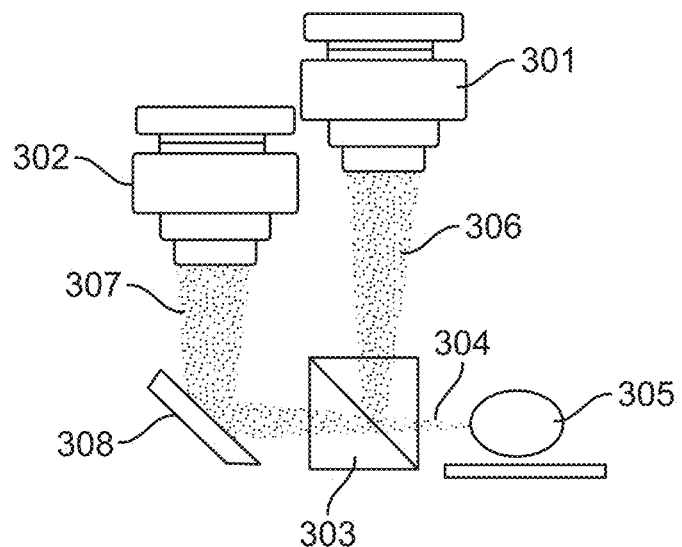
FIG. 3 illustrates a beam splitting configuration in accordance with an embodiment.

FIG. 3 illustrates a beam splitting configuration in accordance with an embodiment. In this configuration, the cameras 301 and 302 remain fixed in place. A beam splitter 303 is used to receive incident light 304 reflecting or emitting from the sample 305 and split the incident light into reflected light 306 and transmitted light 307. The reflected light 306 is captured by the first camera 301, and the transmitted light 307 is captured by the second camera 302 after reflecting off of a mirror 308.

Figure 4:
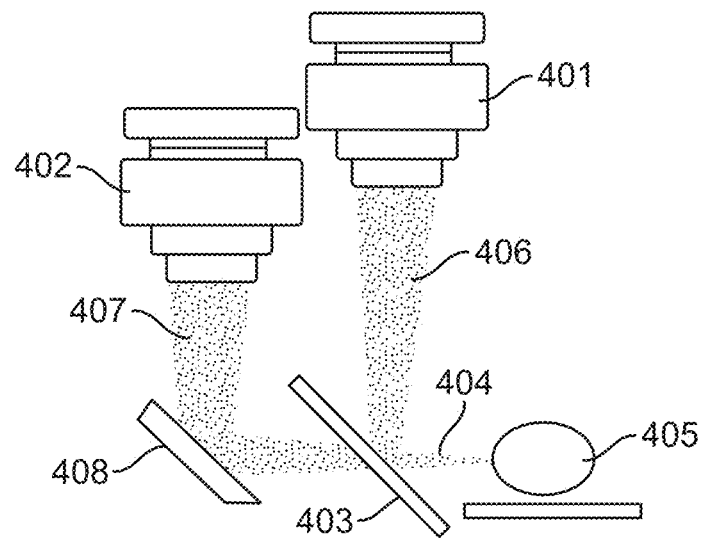
FIG. 4 illustrates a dichroic mirror configuration in accordance with an embodiment.

FIG. 4 illustrates a dichroic mirror configuration in accordance with an embodiment. In this configuration, the cameras 401 and 402 remain fixed in place. A dichroic mirror 403 is used to receive incident light 404 reflecting or emitting from the sample 405 and split the incident light into reflected light 406 and transmitted light 407. The reflected light 406 is captured by the first camera 401, and the transmitted light 407 is captured by the second camera 402 after reflecting off of a fully reflective mirror 408.

The dichroic mirror 403 can be configured to reflect a majority of light outside of a particular range of wavelengths. The dichroic mirror 403 can transmit light within the particular range of wavelengths to camera 402, which can be a cooled monochromatic camera.

Figure 5:
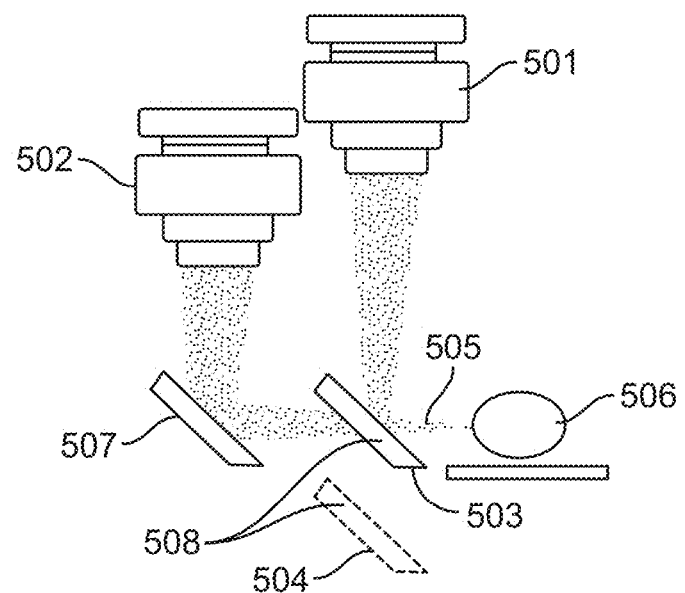
FIG. 5 illustrates a flip mirror configuration in accordance with an embodiment.

FIG. 5 illustrates a flip mirror configuration in accordance with an embodiment. In this configuration, the cameras 501 and 502 remain fixed in place. A fully reflective first mirror 508 can be moved between a first 503 and second 504 position. When the first mirror 508 is in the first position 503, light 505 reflected or emitted by the sample 506 is captured by the first camera 501. When the first mirror 508 is in the second position 504, light 505 reflected or emitted by the sample 506 is reflected by a second mirror 507 and captured by the second camera 502.

In some embodiments, a pivot location offset from the first mirror 508 is used to move the first mirror between its first 503 and second 504 positions. In some embodiments, a slide with detents is used to move the first mirror 508 between its first 503 and second 504 positions, The slide can be made from metal, plastic, or other suitable rigid materials.

Figure 6:
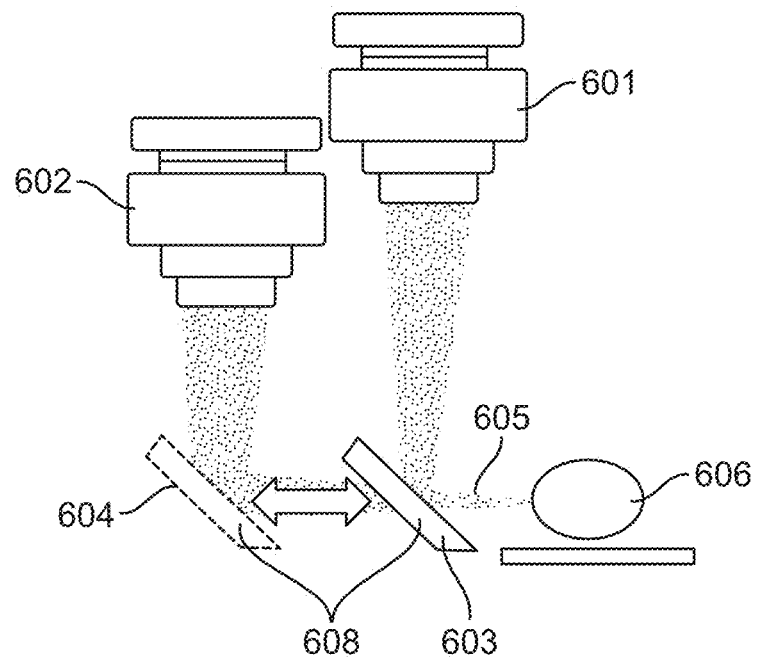
FIG. 6 illustrates a second flip mirror configuration in accordance with an embodiment.

FIG. 6 illustrates a flip mirror configuration in accordance with an embodiment. In this configuration, the cameras 601 and 602 remain fixed in place. A fully reflective mirror 608 can be moved between a first 603 and second 604 position. When the mirror 608 is in the first position 603, light 605 reflected or emitted by the sample 606 is captured by the first camera 601. When the mirror 608 is in the second position 604, light 605 reflected or emitted by the sample 606 is captured by the second camera 602.

In some embodiments, a pivot location offset from the first mirror 608 is used to move the first mirror between its first 603 and second 604 positions. In some embodiments, a slide with detents is used to move the first mirror 608 between its first 603 and second 604 positions, The slide can be made from metal, plastic, or other suitable rigid materials.

In some embodiments, the sample is imaged with a near infrared imaging system that provides a nearly full-rotation 3D tomographic image of surgical samples. The tomographic image can allow for the surgeon and pathologist to efficiently review putative disease areas in an augmented reality display with both fluorescence and reflective imaging modalities. The imaging device can incorporate one or both of true color and fluorescence imaging information with tomographic imaging information. Information associated with each imaging modality can be captured with a nearly 360° sample rotation stage and a 4-degree-of-freedom motion control system.

The nearly full-rotation 3D pseudo-tomography imager can provide an efficient visualization of fluorescence signal at nearly every corner and nearly every facet on a true color 3D sample model. An animation of rotation images representing a 3D reconstructed model displayed on an interactive interface can present to the surgeon and pathologist the results in augmented reality to quickly identify disease areas on a surgical sample such as a tumor margin or biopsy.

The proposed near-infrared (NIR) fluorescence pseudo-tomography imaging system comprises an NIR optical engine for excitation and image collection, a pseudo tomography platform for sample positioning to generate 3D images, a sample delivery system to optimize throughput, and an interactive user interface for efficient image review.

Short wavelength NIR imaging around 700 to 800 nm has been well accepted in research applications due to advantages such as the availability of clinical and translational optical agents, high signal-to-noise ratios, low native tissue/bio-material fluorescence (autofluorescence), and low extinction at the excitation and emission wavelengths. Commercial products have been developed for small animal fluorescence imaging in the NIR range.

The imaging system optical engine can also include laser sources in dual directions, white light LED illumination, specialized filter systems, a cooled imaging camera, and noise suppression technology. The laser sources can have wavelengths of, for example, one or more of 488 nm, 512 nm, 533 nm, 550 nm, 580 nm, 633 nm, 650 nm, 675 nm, 690 nm, 743 nm, 785 nm, or 806 nm. In some embodiments, the laser sources are 690 nm and 785 nm for 700-nm and 800-nm channels, respectively. LED illumination can have wavelengths in one or more ranges from 450 nm to 850 nm, from 450 nm to 650 nm, from 550 nm to 750 nm, from 650 nm to 850 nm, from 450 nm to 550 nm, from 500 nm to 600 nm, from 550 nm, to 650 nm, from 600 nm to 700 nm, from 650 nm to 750 nm, from 700 nm to 800 nm, or from 750 nm to 850 nm. In some embodiments, the LED illumination is at 670 nm and 760 nm for NIR dye excitation. In some embodiments, the LED illumination is broad band illumination at visible wavelengths for white light illumination. Filter sets are designed to isolate excitation wavelength(s) with optimized emission collection for corresponding imaging agents (i.e. IRDye 800CW and ICG).

The imaging system can offer high dynamic range and optimized signal-to-noise ratios with uniform illumination of the imaging field. The imaging dynamic range can be >6 logs (22-bit) in one imaging capture cycle. This dynamic range is higher than those (8-16 bit) commonly offered by other fluorescence imaging technologies. To relieve the processing loads from high dynamic range imaging, one can apply floating point values (instead of long integer values) for each pixel to maximize dynamic range without increasing image size. Thus imaging and processing speed is competitive.

In some embodiments, dark noise calibration is used to give imaging results high signal linearity for quantifiable evaluation. For example, testing on subcutaneous tumors (IRDye 800CW-labeled agent, 15 nmol) of a mouse model has demonstrated linear imaging signal versus tumor tissue weight (Pearson $r=0.97$ with $P$-value$<0.0001$).

In some embodiments, uniform illumination and field flattening correction technologies for laser(s) and LED (light emitting diode) white light channels are used to ensure the reliability and reproducibility of imaging throughout the whole imaging field. The uniformity and reliability can be such that coefficients of variation of approximately 0.04% are observed for repeated measurements at the same positions and <3% for measurements at different positions in the illumination field.

In some embodiments, a pseudo-tomography imager can be capable of detecting indocyanine green (ICG), IRDye 800CW, and other dyes with emission in the 800-nm range. ICG is a clinically approved NIR fluorescence imaging contrast agent. In a dilute aqueous solution, ICG shows an absorption peak around the wavelength 780 nm and an emission peak around 822 nm.

As a systemically administered imaging contrast agent, ICG offers a favorable safety profile and has been approved by U.S. Food and Drug Administration (FDA) for imaging of lymphatic flow, evaluation of hepatic function and liver blood flow, cardiac output, and other indications. Clinical trials for intraoperative imaging of tumors with ICG have been conducted on a variety of cancers. The use of ICG in tumor detection may be limited because ICG does not contain a reactive functional group for conjugation to target molecules specific to tumor tissues. Nevertheless, clinical studies show ICG may be beneficial for tumor tissue localization in sentinel lymph nodes and in liver, due to pooling effects of dye in the lymphatic system and uptake of ICG by hepatic parenchymal cells in liver. Focal accumulation or fluorescent rim in hepatocellular carcinoma can be visualized by an embodiment imaging device to indicate regions of interest in resected tissues prior to frozen analysis for intraoperative consultation. As the only NIR imaging agent currently approved by FDA, ICG permits rapid clinical translation of the proposed imaging device to intraoperative consultation.

LI-COR's IRDye 800CW has been used in clinical studies and trials for the detection of tumors. It offers reactive groups for easy conjugation with antibodies and superior solubility in aqueous solutions. IRDye 800CW advantages include that the dye is manufactured under cGMP and suitable for human use currently in investigational studies. A rodent toxicity study with IRDye 800CW carboxylate showed no toxic effects under the conditions of the study. A non-human primate toxicity study was completed in 2013 and showed no clinically significant toxicities from cetuximab-IRDye 800CW. Multiple human studies and clinical trials of IRDye 800CW-conjugates as imaging agents are being conducted. To date, the study results and clinical trial outcomes with IRDye 800CW-conjugates are encouraging.

FDA approved anti-epidermal growth factor receptor (EGFR) monoclonal antibodies, cetuximab and panitumumab, and anti-vascular endothelial growth factor (VEGF) antibody, bevacizumab, have been conjugated to IRDye 800CW for tumor targeted imaging. A systemic dose escalation study has shown safety and efficacy in a clinical trial. Other similar moieties can also be attached to the dye. Some of these additional moiety attachments can also be undergoing current clinical trials.

Sensitivity and specificity (reducing false negatives) are key metrics to validate the imaging technologies applied in a 3D imager. One study demonstrated that the presently disclosed imaging module can produce superior sensitivity, specificity, detection limits and signal contrast. In this study, nude mice (Charles River Lab) received HNSCC (head and neck squamous carcinoma) cells to generate xenograft tumors. Imaging experiments were performed 48-96 hours following a systemic injection of panitumumab-IRDye 800CW. IgG-IRDye 800CW was used to assess non-specific binding. It was shown that the new imaging technology gives high tumor-to-background ratio with low nonspecific or native fluorescence background. The high contrast and tumor-to-background ratio is due at least in part to linear background suppression, high dynamic range technologies, and other imaging advances.

In some embodiments, a substantially uniform illumination area (3% variation) and imaging depth of focus will accommodate a 3-inch cube with resolution of ~125 µm. Other embodiments establish an imaging volume of a >4-inch cube.

In contrast with conventional small animal fluorescence imaging which provide images of partial 3D faces, the disclosed systems, devices, and methods can offer nearly full 3D imaging, presenting nearly full or Euler animated rotations of the resulting reconstructed model. In some embodiments, the pseudo-tomography imager provides fluorescence imaging and reflective white light imaging co-localized in a nearly full-rotation 3D image.

In some embodiments, a tomography platform is coordinated with the optical engine to provide the nearly full-rotation 3D imaging result. The imaging volume of the tomography system is a 3D space that accommodates the resected tissue sample. The imaging volume of this system is defined by the illumination fields of the excitation light, the depth of focus of the objective, and the field of view of the imaging head. The imaging volume can have a depth (in the x-axis) of, for example, 1 inch, 1.5 inches, 2 inches, 2.5 inches, 3 inches, 3.5 inches, 4 inches, 4.5 inches, or 5 inches. The imaging volume can have a cross-section (in the x-y plane) of, for example, $7 \times 8$ cm$^2$, $7 \times 10$ cm$^2$, $7 \times 12$ cm$^2$, $8.5 \times 8$ cm$^2$, $8.5 \times 10$ cm$^2$, $8.5 \times 12$ cm$^2$, $10 \times 8$ cm$^2$, $10 \times 10$ cm$^2$, or $10 \times 12$ cm$^2$. The imaging resolution can be, for example, about 50 line pairs per inch, about 60 line pairs per inch, about 70 line pairs per inch, about 80 line pairs per inch, about 90 line pairs per inch, about 100 line pairs per inch, about 110 line pairs per inch, about 120 line pairs per inch, about 130 line pairs per inch, about 140 line pairs per inch, about 150 line pairs per inch, about 200 line pairs per inch, about 250 line pairs per inch, about 300 line pairs per inch, about 350 line pairs per inch, about 400 line pairs per inch, about 450 line pairs per inch, about 500 line pairs per inch, about 550 line pairs per inch, or about 600 line pairs per inch.

The tomography platform is equipped with rotational motors and stages to control the view angle and position of a sample within the imaging volume. By rotating a sample in two degrees of freedom, an imager can efficiently provide a nearly full rotation 3D image. The first rotation is a nearly 360-degree movement along the z-axis (roll) relative to the sample to collect images at serial view angles. The second rotation is tilting along y-axis (pitch) for imaging at different perspectives. Tilting of the sample stage allows projection views from the top and bottom of the sample via a transparent glass window. Rotation combinations allow nearly the entire sample to be imaged. Translational movements of the sample stage in X-Y plane allow the registration of the sample to the center of the imaging volume.

To collect pertinent imaging projections along a sample for 3D reconstruction, the tomography platform rotates the object in two degrees-of-freedom. To provide comprehensive coverage of sample features, the tilting angle is typically in the range from 7.5 degrees to 45 degrees, depending on the complexity of the sample. With sample holding structures, such as pins, clamps, or stops, larger tilting angle can be achieved. A rolling step of 22.5 degree and a tilting angle at ±35 degrees in an embodiment can offer a nearly full rotation animation for 3D inspection.

For many practical applications, an imaging device should be capable of imaging a tissue having a size of ~3-inch diameter or larger with resolution better than 150 µm. The sample stage can be designed with lightweight material to accommodate large samples. In some embodiments, the sample stage has a custom-made glass window with marking dimensions at its edges.

In some embodiments, the sample to be imaged is supported by a platform or stage having a transparent portion or window. In some embodiments, the entire platform or stage is transparent.

Figure 7:
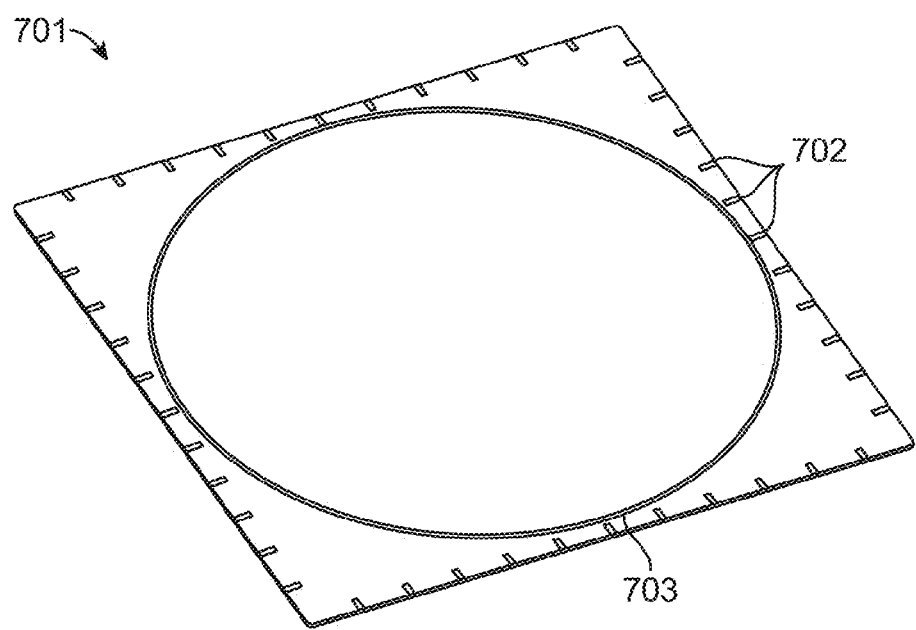
FIG. 7 illustrates transparent window with scale marks in accordance with an embodiment.

FIG. 7 illustrates a transparent window 701 for object registration in accordance with an embodiment. The window 701 is marked with scale marks 702 and a circle 703. The circle 703 marks the suggested border within which a sample to be imaged should be placed.

The window can be transparent at the working wavelengths for both reflective light and fluorescence imaging. To accommodate a large size sample, the window can be custom made to a shape that is wider than the projection size of the imaging volume or the footprint of a target sample.

The material of the window can be borosilicate based glass, or other transparent material. The surface could be treated or coated for optical (anti-reflection, transparency, absorption purposes) or surface functional (hydrophobic or hydrophilic properties, marks, barcodes, etc.) requirements.

A circle on the window can be used to mark the border of suggested imaging area. Tick marks along the window can provide reference scales to users. The tick marks also can allow the construction software to identify and calculate the dimensions with references extending into the spatial volume.

Figure 8:
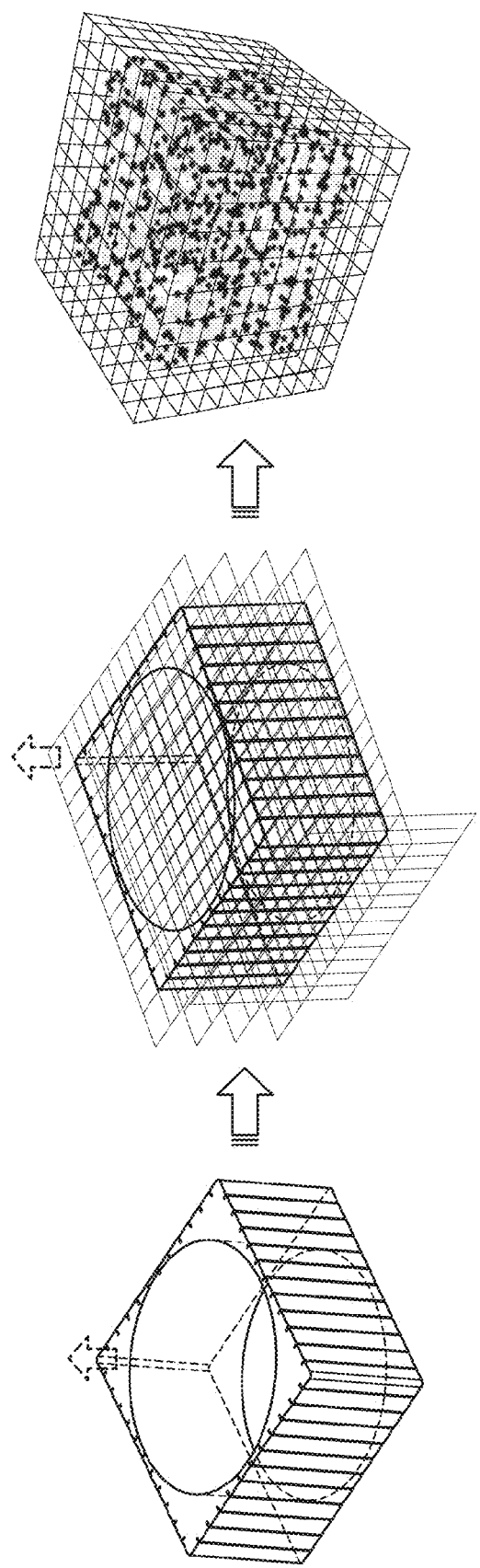
FIG. 8 illustrates using the use of scale marks on the transparent window of FIG. 7 for object registration in accordance with an embodiment.

FIG. 8 (left side) illustrates the virtual reference marks extended from the glass window surface at a known rotation angles (along x, y, and z axis). The scale references can be used to help the software to recognize the dimension of an object. In the middle figure, the software is shown to be able to generate precise 3D grids and sub-volumes. The information at each projection view and each view angle allows the software to label the dimension, position, points, features, voxels at different facets of a sample. In the rightmost figure of FIG. 8, with the information from a deck of rotation angles, the generated 3D grid renders the interception points of an object inside the confined virtual volume. The information assists the reconstruction of the object and the rendering of signal distributions.

Due to the divergent propagation of excitation light along the depth of imaging volume (x-axis), the imaging analysis may need to apply a correction factor in volume to compensate for decay along the sample.

Figure 9:
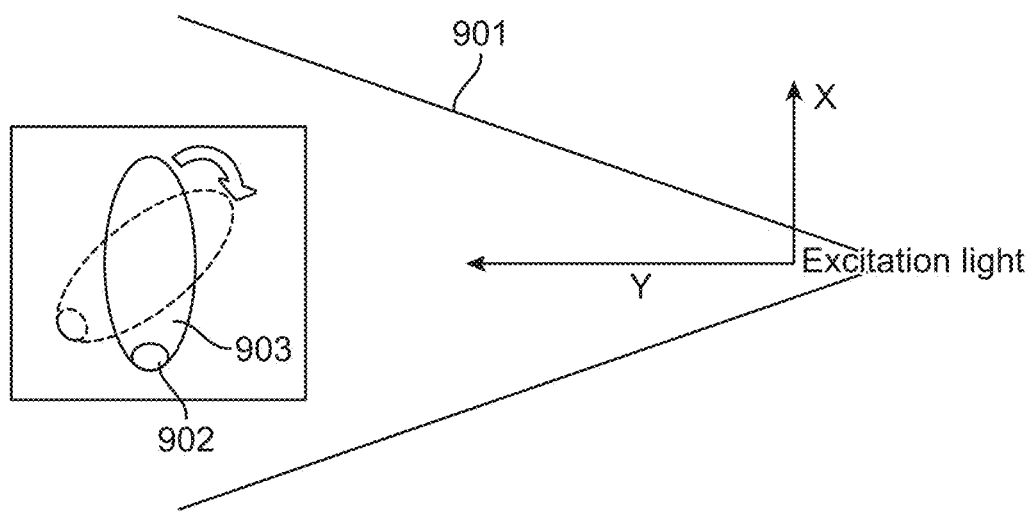
FIG. 9 illustrates fluorescence image correction of a rotated sample in accordance with an embodiment.
Figure 10:
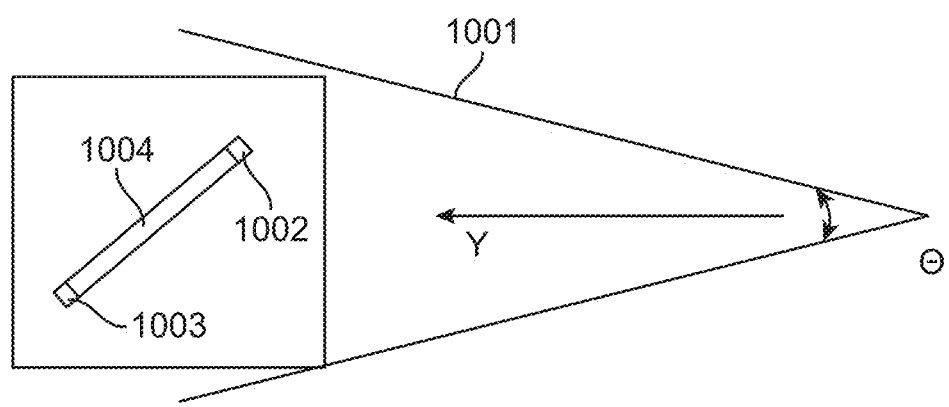
FIG. 10 illustrates fluorescence image correction of two points on a sample in accordance with an embodiment.

FIGS. 9 and 10 illustrate fluorescence image corrections of a rotated sample at one or two points, respectively, in accordance with an embodiment. FIG. 9 demonstrates that the excitation intensity of a divergent beam 901 at a signal spot 902 on an object 903 varies when the object rotates or moves to a different position. FIG. 10 demonstrates that a controlled diverging light 1001 would give different excitation energy density at a first 1002 and second 1003 spot on an object 1004 because the distances from the excitation source to the spots are different even absent rotation of the object.

For large-area illumination, the excitation light goes along the propagation axis towards an object with controlled divergence or defined illumination pattern. In the figures, the excitation radiation comes from a point source and is diverging toward the imaging volume for fluorescence excitation. If a signal spot is located at one end of an object, the energy density of the excitation wavefront at the area of the signal spot varies as the object is rotated to a different view angle. For a point source (isotropic radiator), the energy density at a distance y follows the inverse-square law ($I=1/y^2$). For a controlled divergence to achieve uniform illumination at an x-y plane, the function of light intensity along the propagation axis can be specified or can be measured. With a known function of energy density at a distance y, a correction factor can be applied into the signal reconstruction model. The 3D information collected via the reflective light imaging gives the geometric information at the spots of interest. The correction factor of fluorescence signal can then be implemented to improve the reliability and quantifiability of the imaging result. For a complicated model, scattering and extinction of the signal light going through a part of the tissue object can be considered to further improve the fidelity of reconstructed results under superficial layers.

In some embodiments, a tomographic imager can generate a series of images corresponding to different view angles automatically in short period of time. Collocated serial images of two modalities are obtained by overlaying images of reflective light and fluorescence together. Software code is used to compile the serial imaging results into an animation to demonstrate the nearly full-rotation 3D views of a sample. The animation offers real-time 3D perspectives of nearly the entire sample. For the 3D reconstruction of the sample model and the interactive displaying of the 3D results, commercial 3D reconstruction algorithms can be used.

In some embodiments, the imaging process of an entire sample at 85 µm resolution can be done in 20 min or less. In some embodiments, a 3D animation can be generated within a minute or less.

Figure 11B:
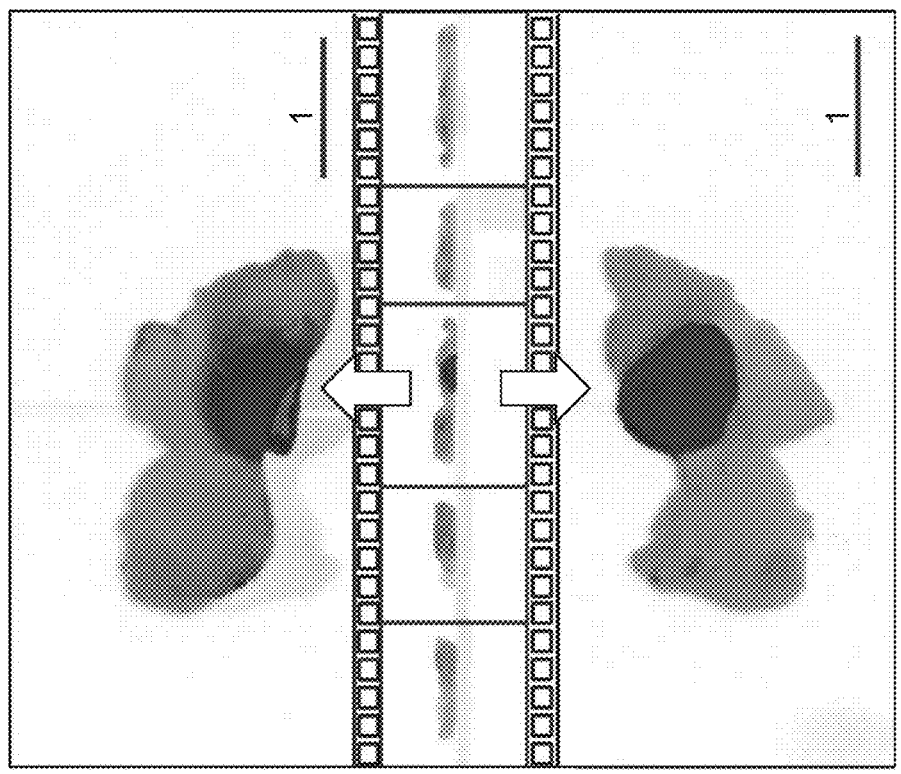
FIG. 11B illustrates a filmstrip view of 3D animation presenting images of the tumor of FIG. 11A in accordance with an embodiment.
Figure 11A:
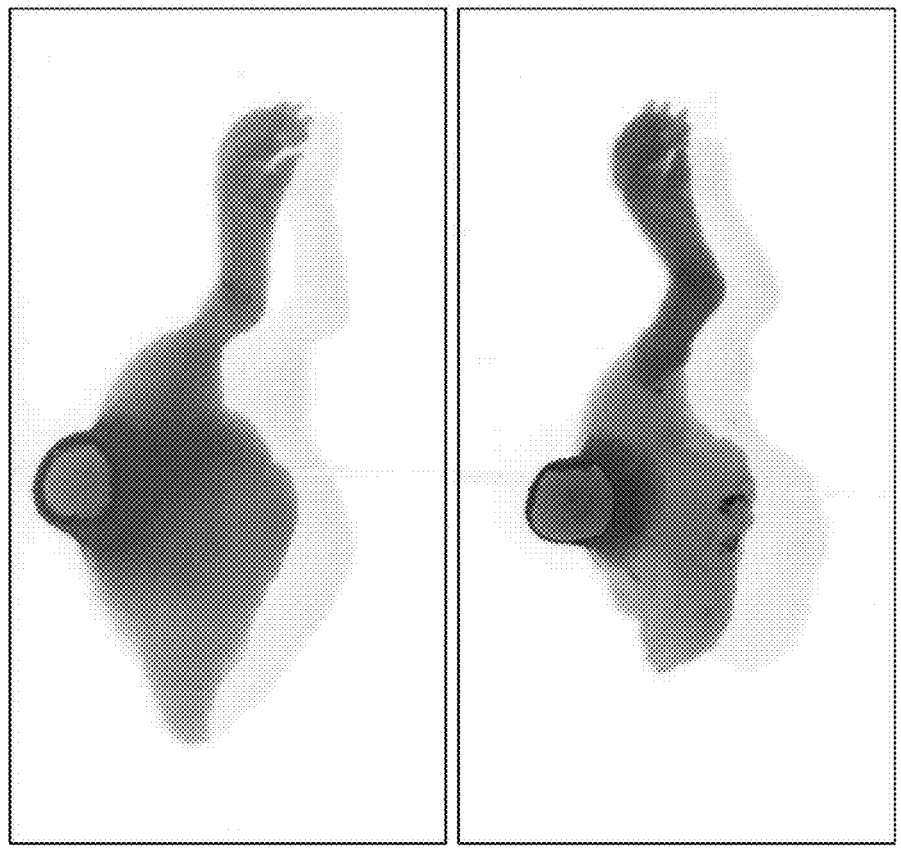
FIG. 11A illustrates images of xenograft tumor tissue.
Figure 12:
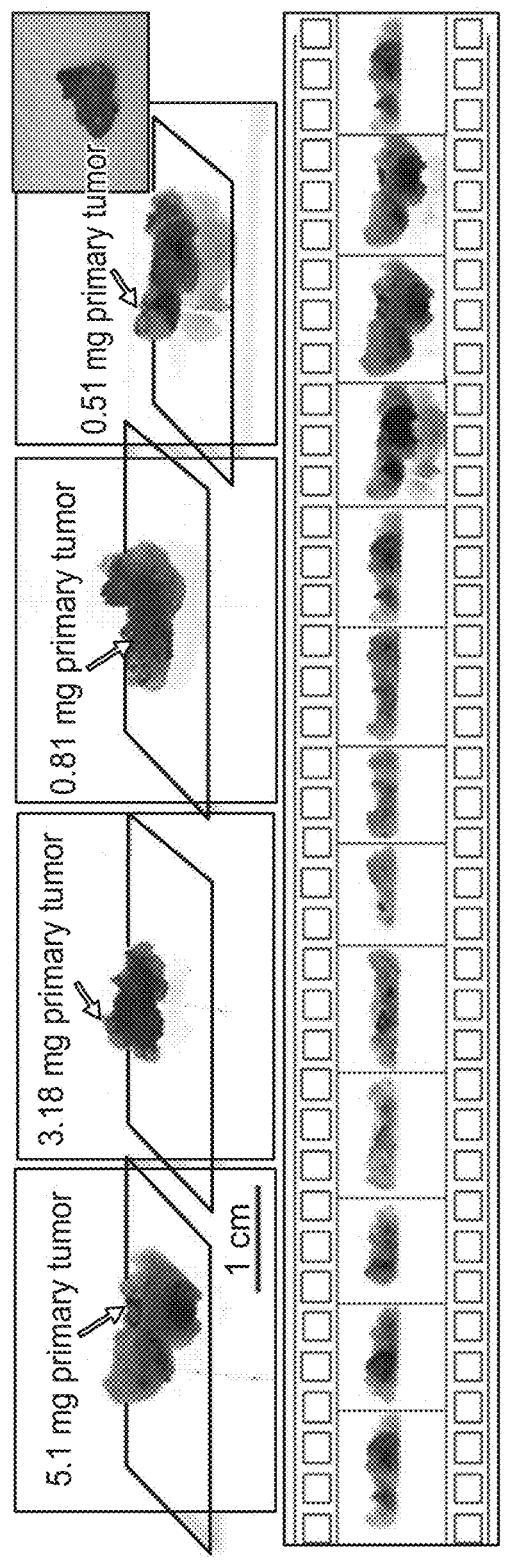
FIG. 12 illustrates the imaging of different tumor sizes and a filmstrip presentation manner of a graphical user interface (GUI) in accordance with an embodiment.

FIGS. 11-13 illustrate a GUI and its touch screen manipulation in accordance with an embodiment. A tablet display can be used by a user to browse views interactively in two rotation axes (roll and pitch). In addition to a frame rate of 3-10 frames/second, which may be changeable for a dynamic animation preview, a user can scroll among different frames on a touch screen for static review of each frame with zoom-in up to 5-fold, (~12.5 µm/pixel display resolution) for detailed inspection. This can further help sample inspection and disease tissue localization.

In FIGS. 11A and 11B, a nearly full-rotation imaging display is used to localize disease tissue. In FIG. 11A, a 3D imaging result of a xenograft tumor tissue on a mouse limp with (upper panel) and without (bottom panel) skin is shown. In FIG. 11B, an example of selected 3D animation shows that the top and bottom views of a full rotation 3D imaging result help localize the disease tissue. A pseudo color map for fluorescence is provided.

In FIG. 12, example images of human samples to evaluate the minimal amount of detectable tumor are shown. The upper row of FIG. 12 shows images of tissues collected from a systemic labeled patient cohort. The bottom row of FIG. 12 shows images of selected 3D rotation animation frames from an example 3D visualization result. A pseudo color map for fluorescence is provided. Gray scale is for reflective light.

Figure 13B:
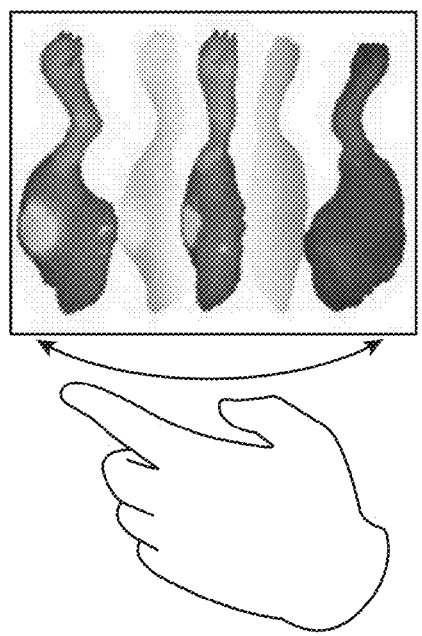
FIG. 13B illustrates touch screen manipulation of a GUI in a pitching mode in accordance with an embodiment.
Figure 13A:
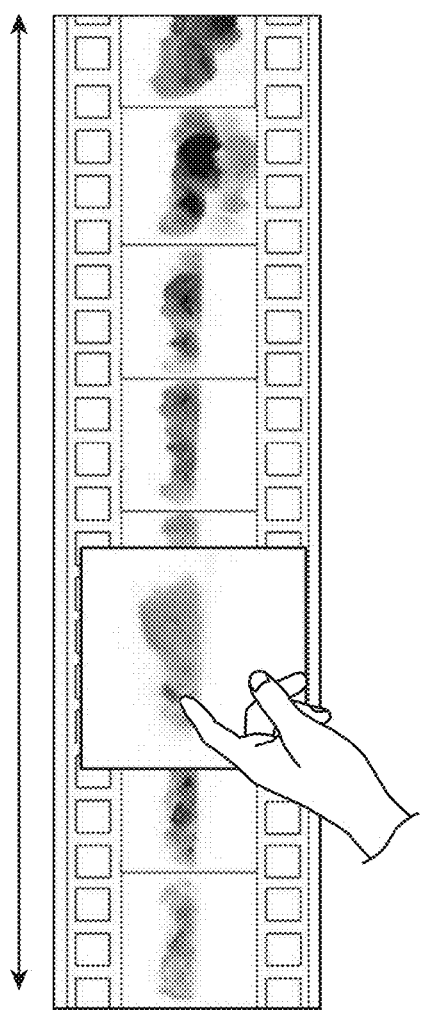
FIG. 13A illustrates touch screen manipulation of a GUI in a rolling mode in accordance with an embodiment.
Figure 14:
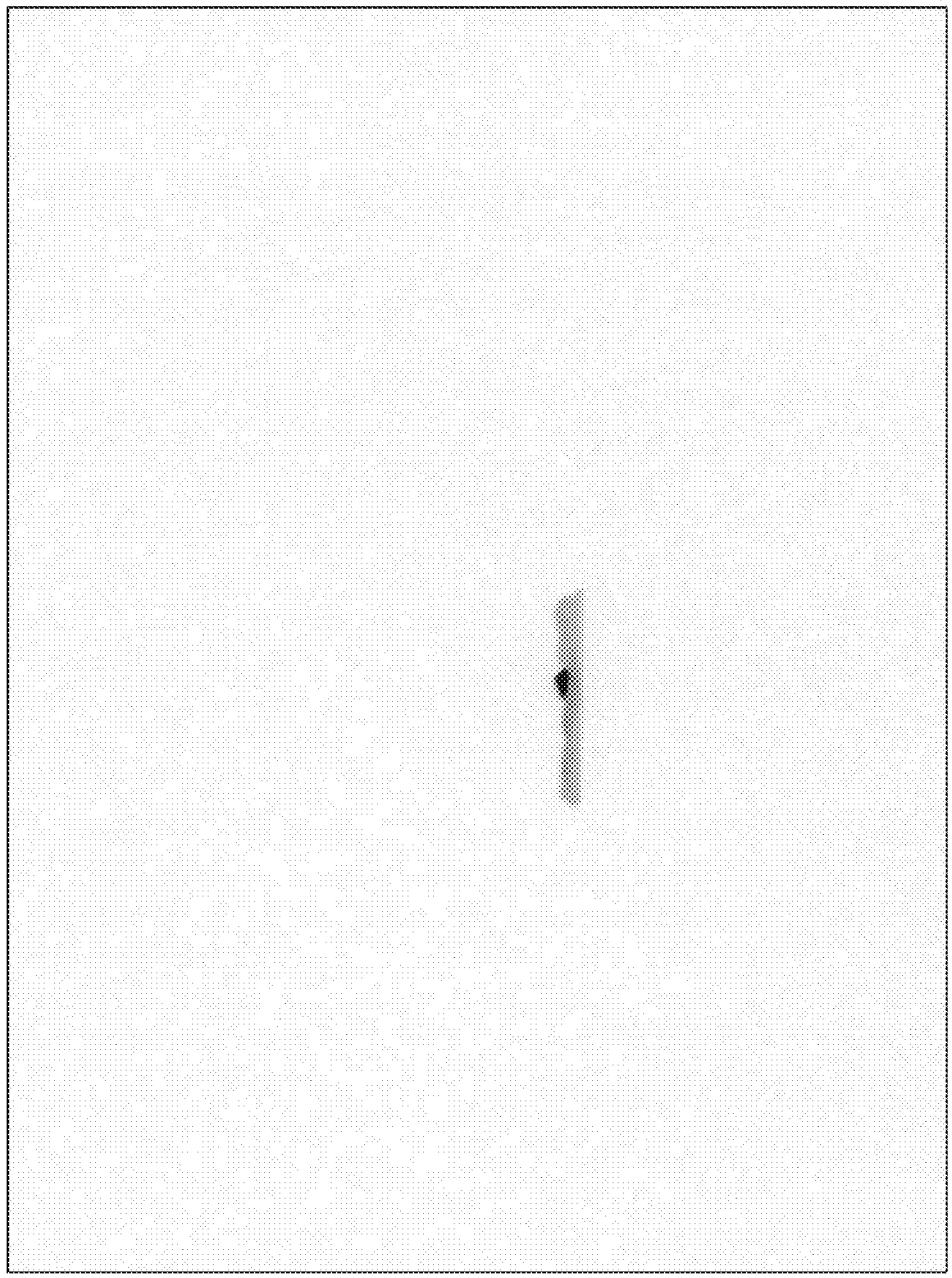
FIGS. 14-41 illustrate overlaid full-color and fluorescence images of an object at different angles in accordance with an embodiment.
Figure 15:
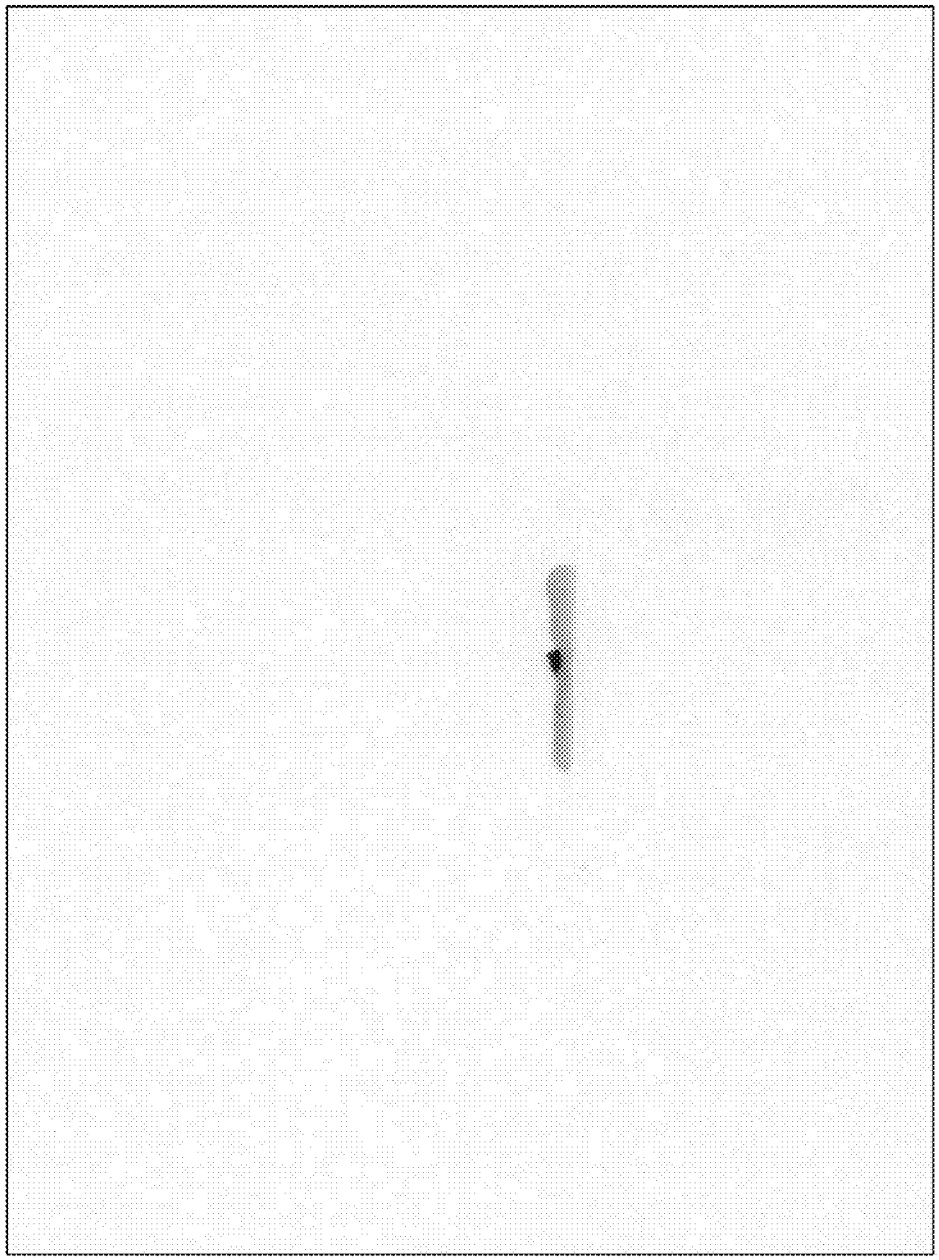
Figure 16:
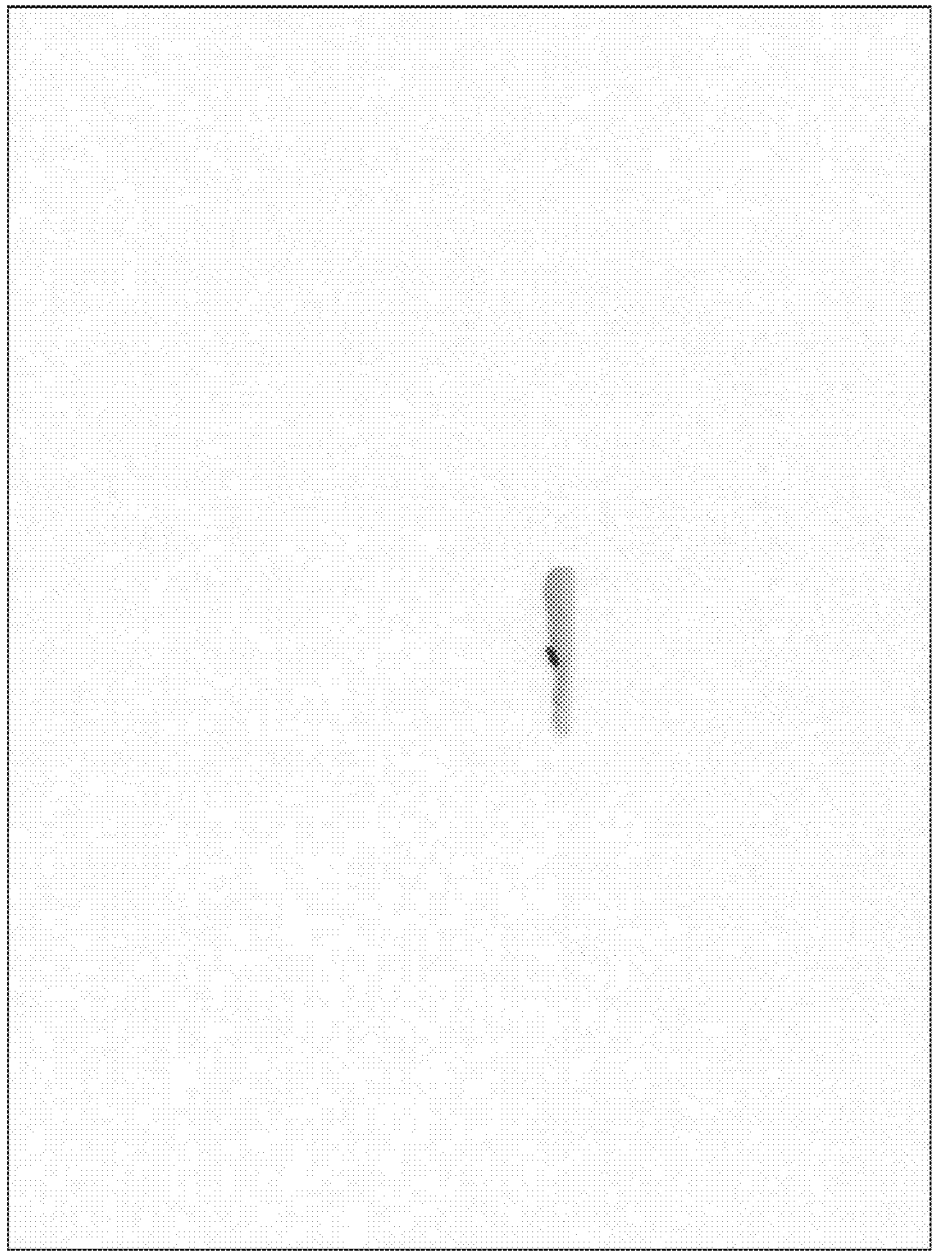
Figure 17:
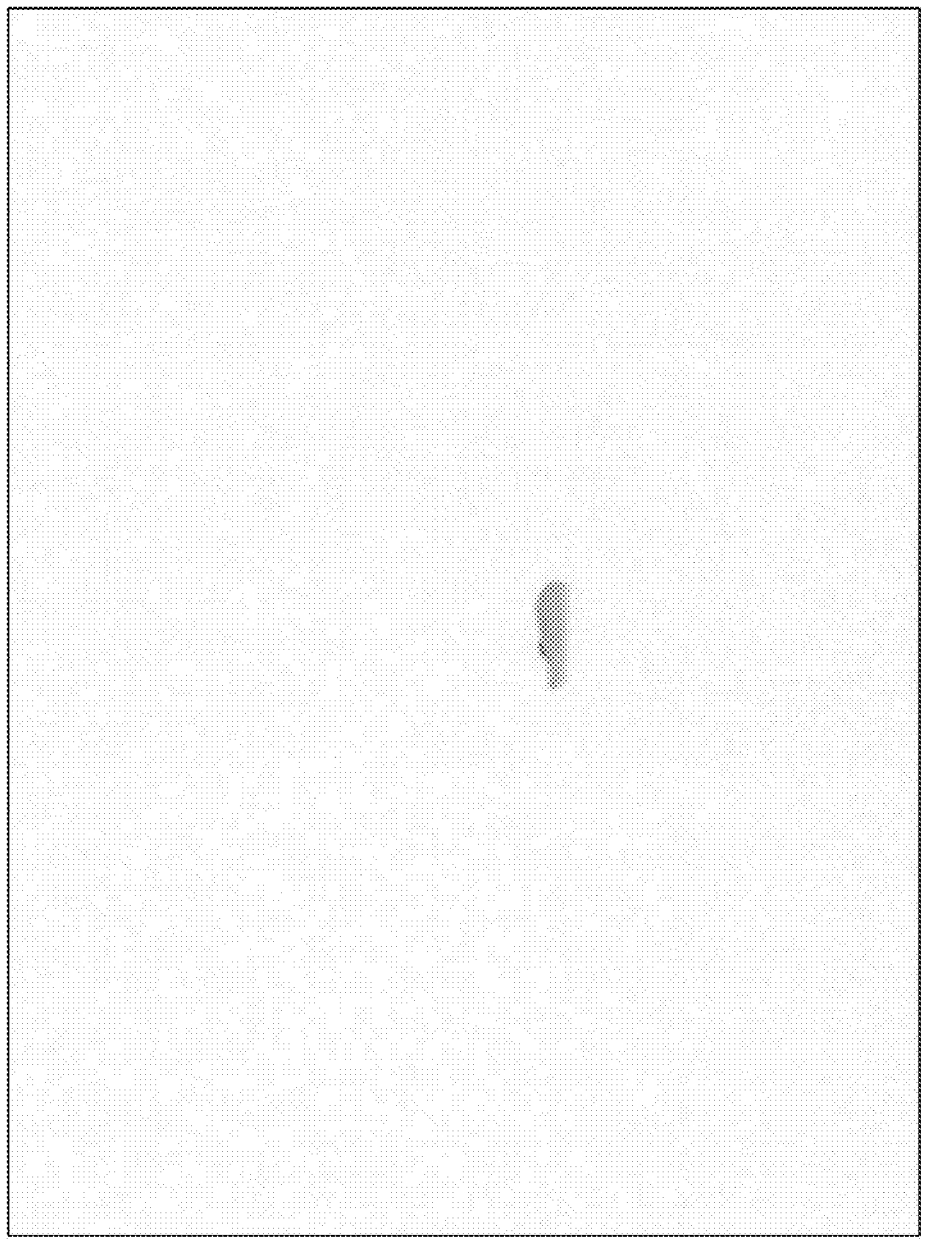
Figure 18:
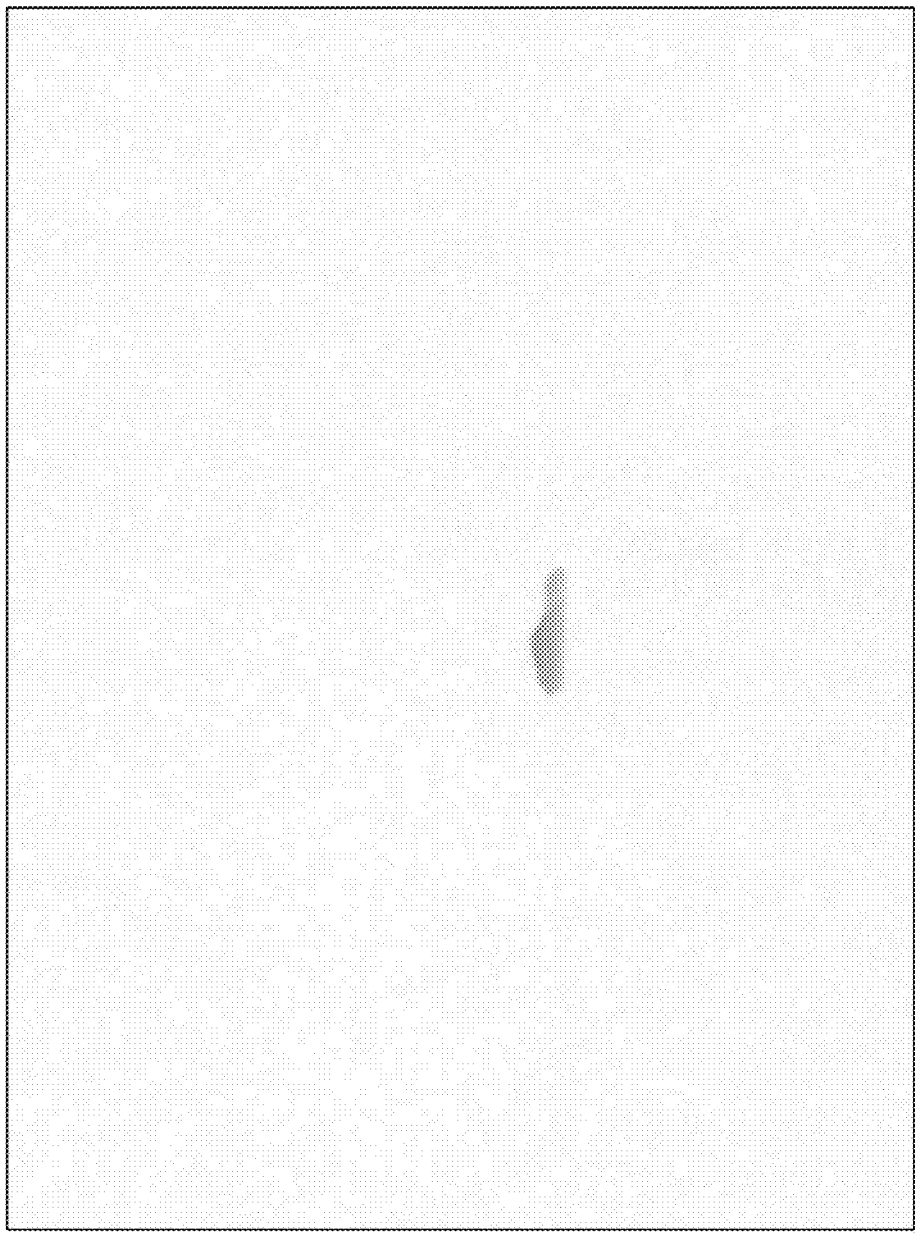
Figure 19:
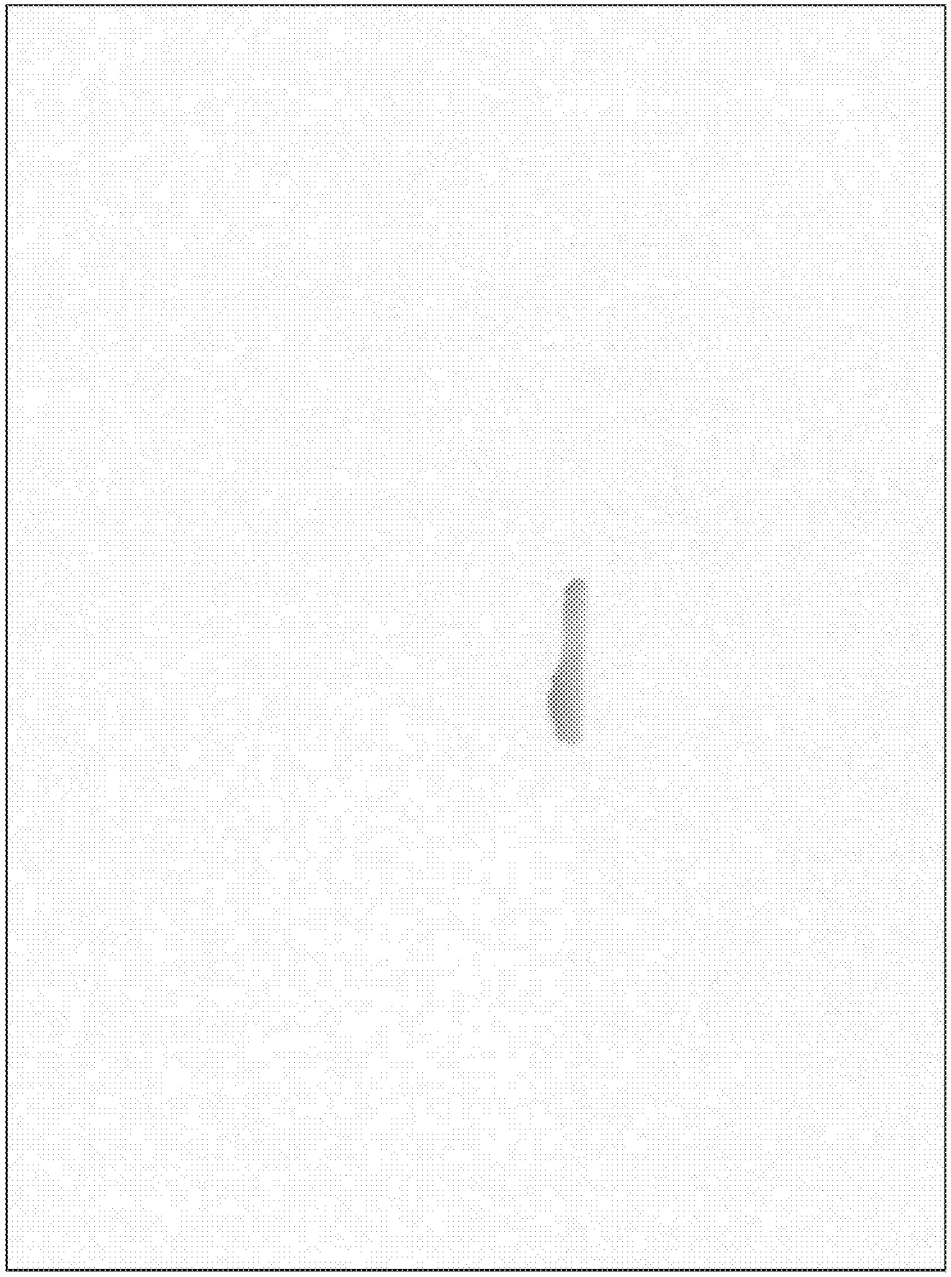
Figure 20:
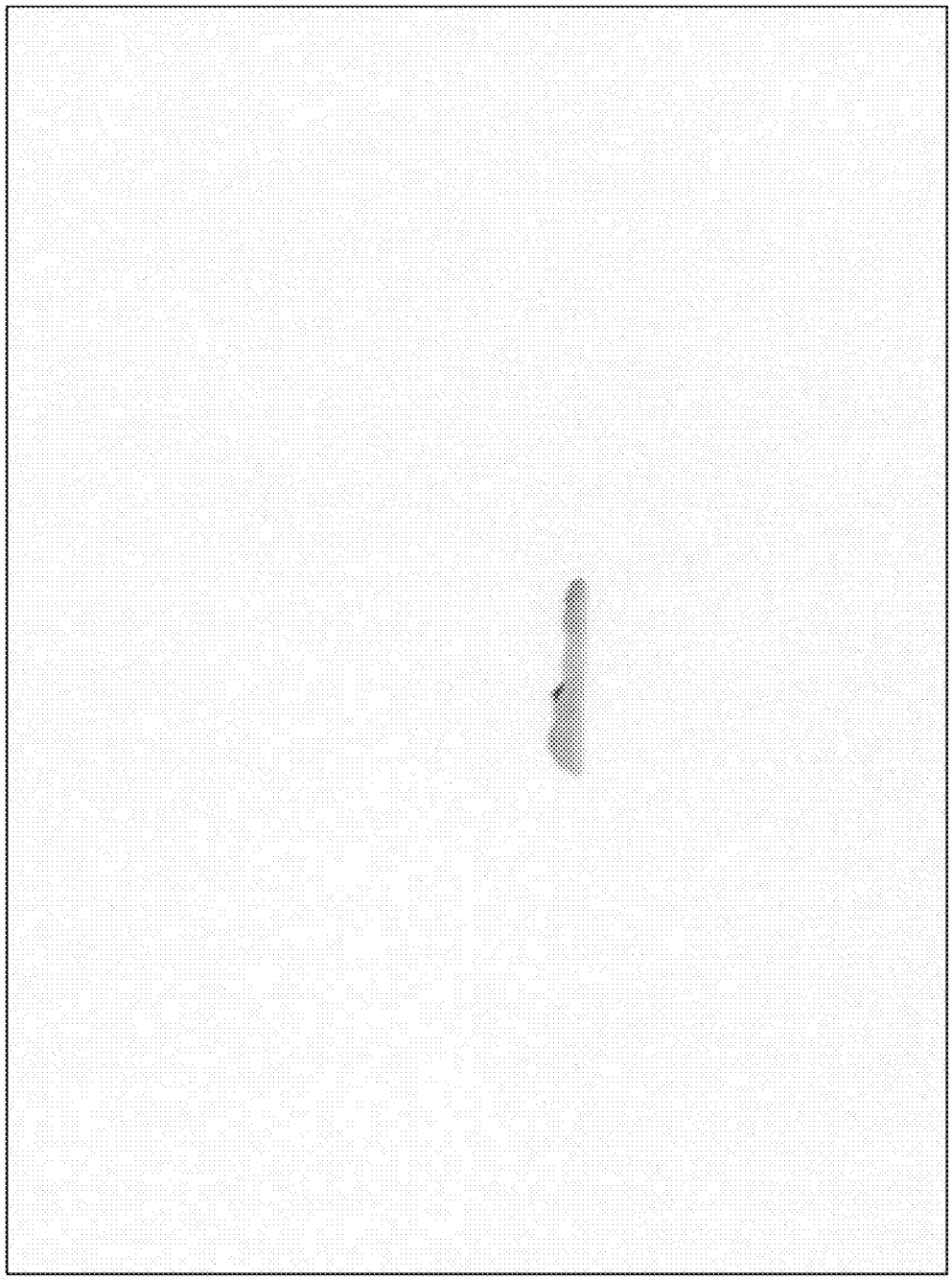
Figure 21:
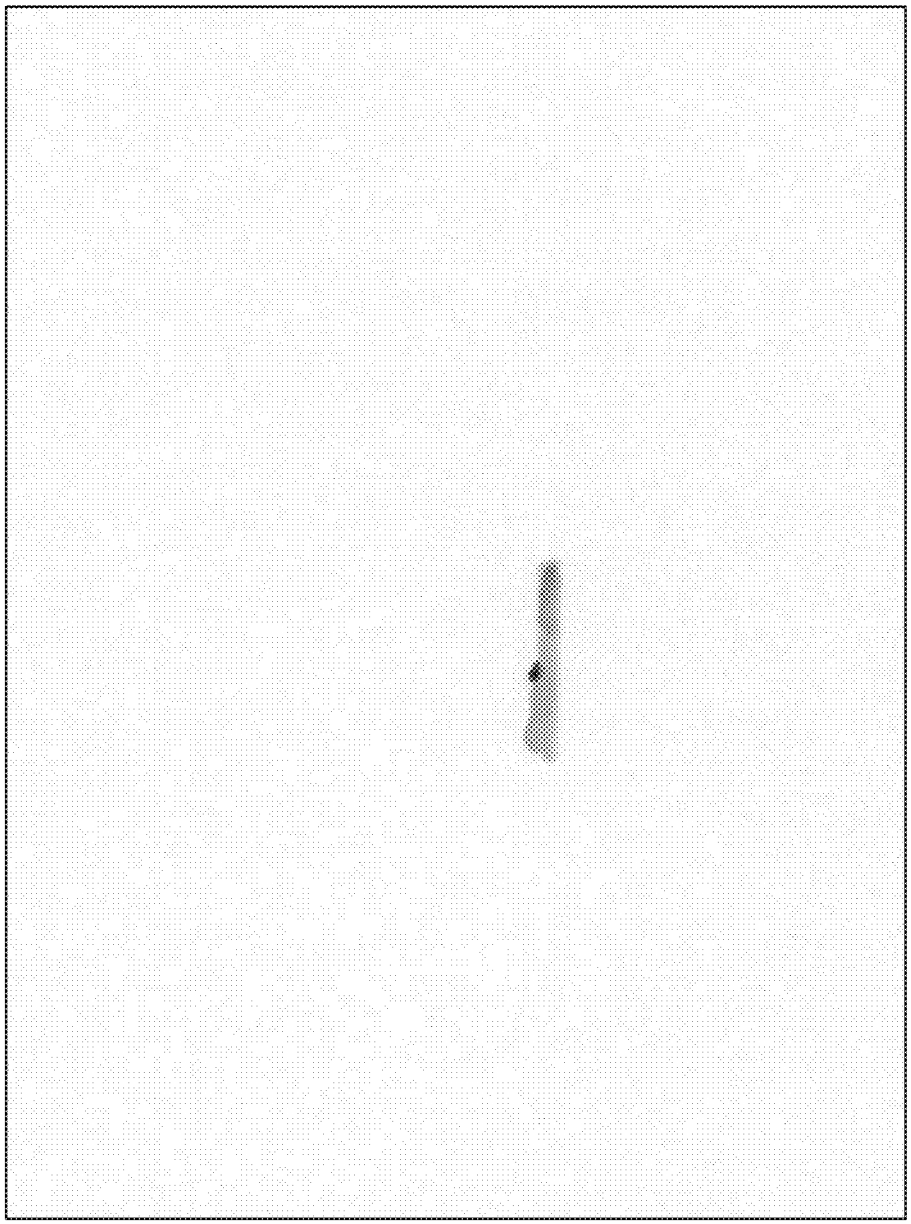
Figure 22:
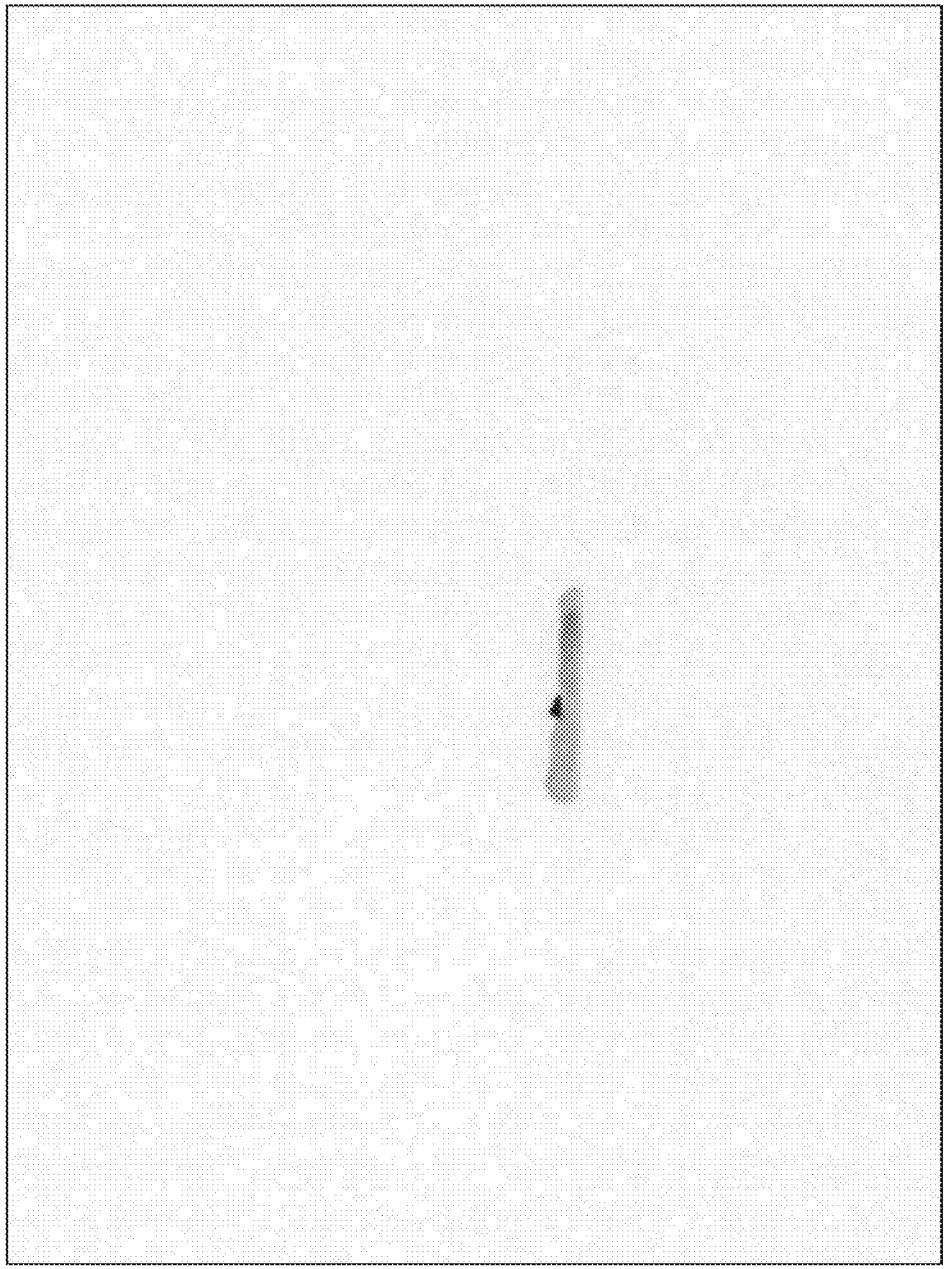
Figure 23:
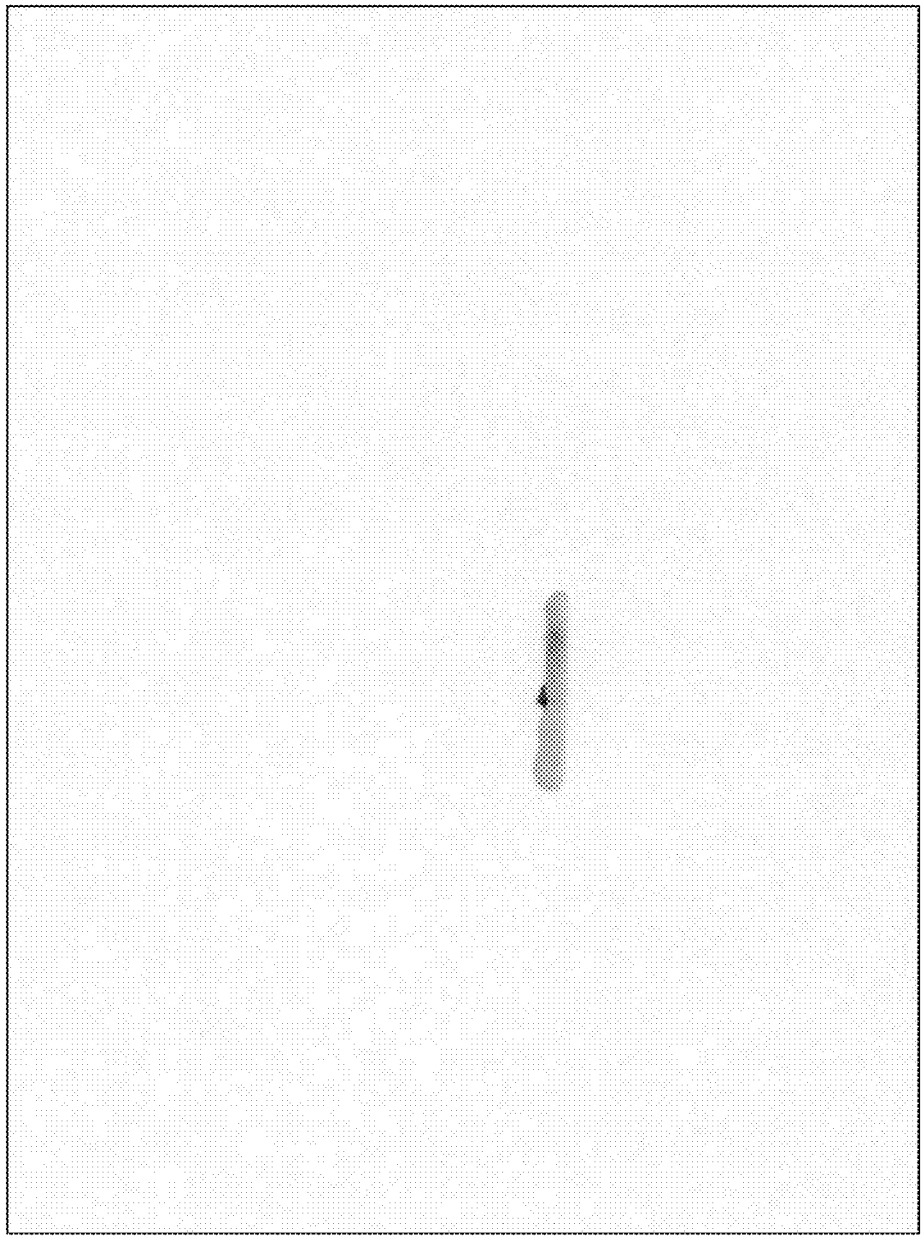
Figure 24:
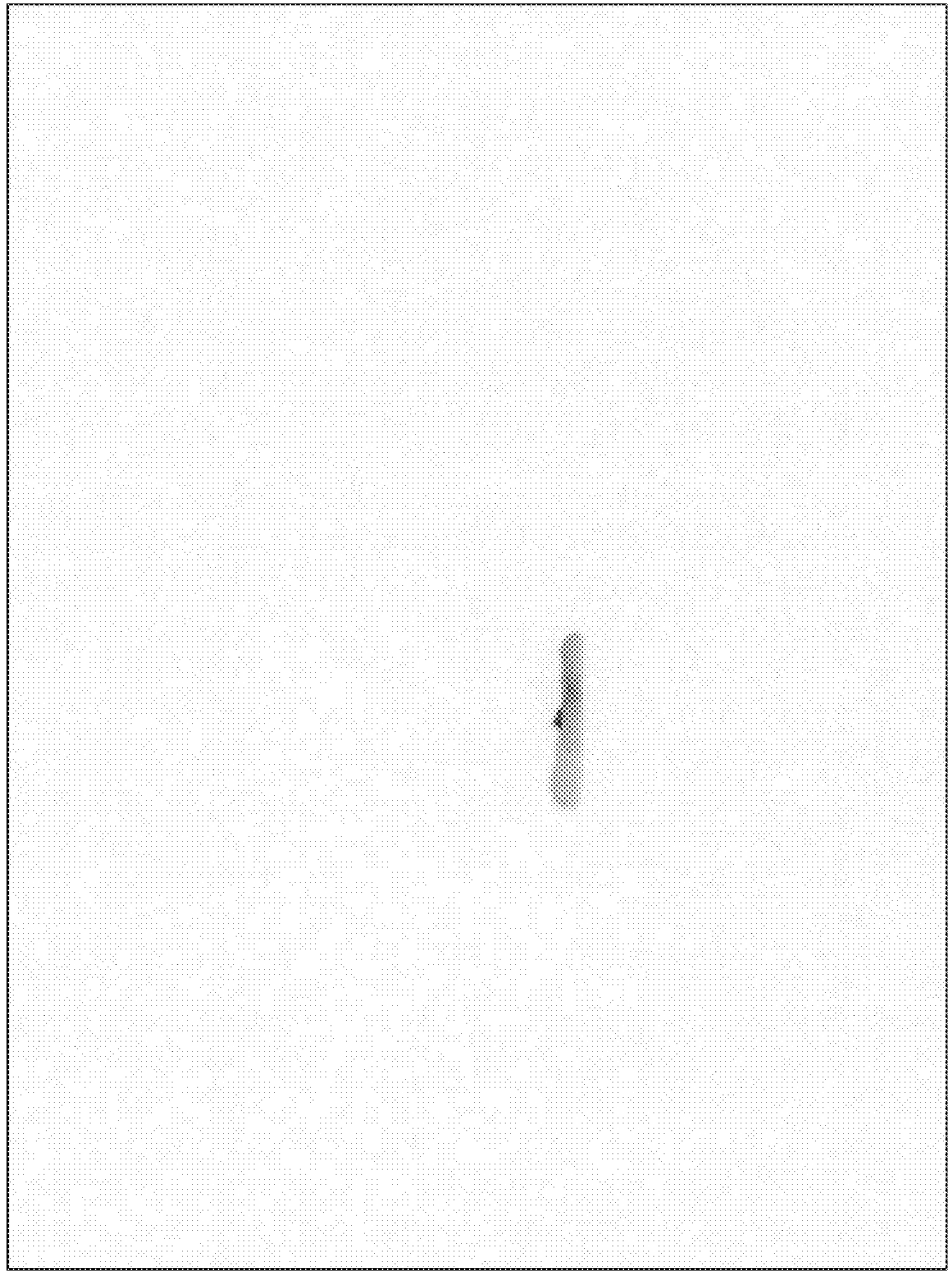
Figure 25:
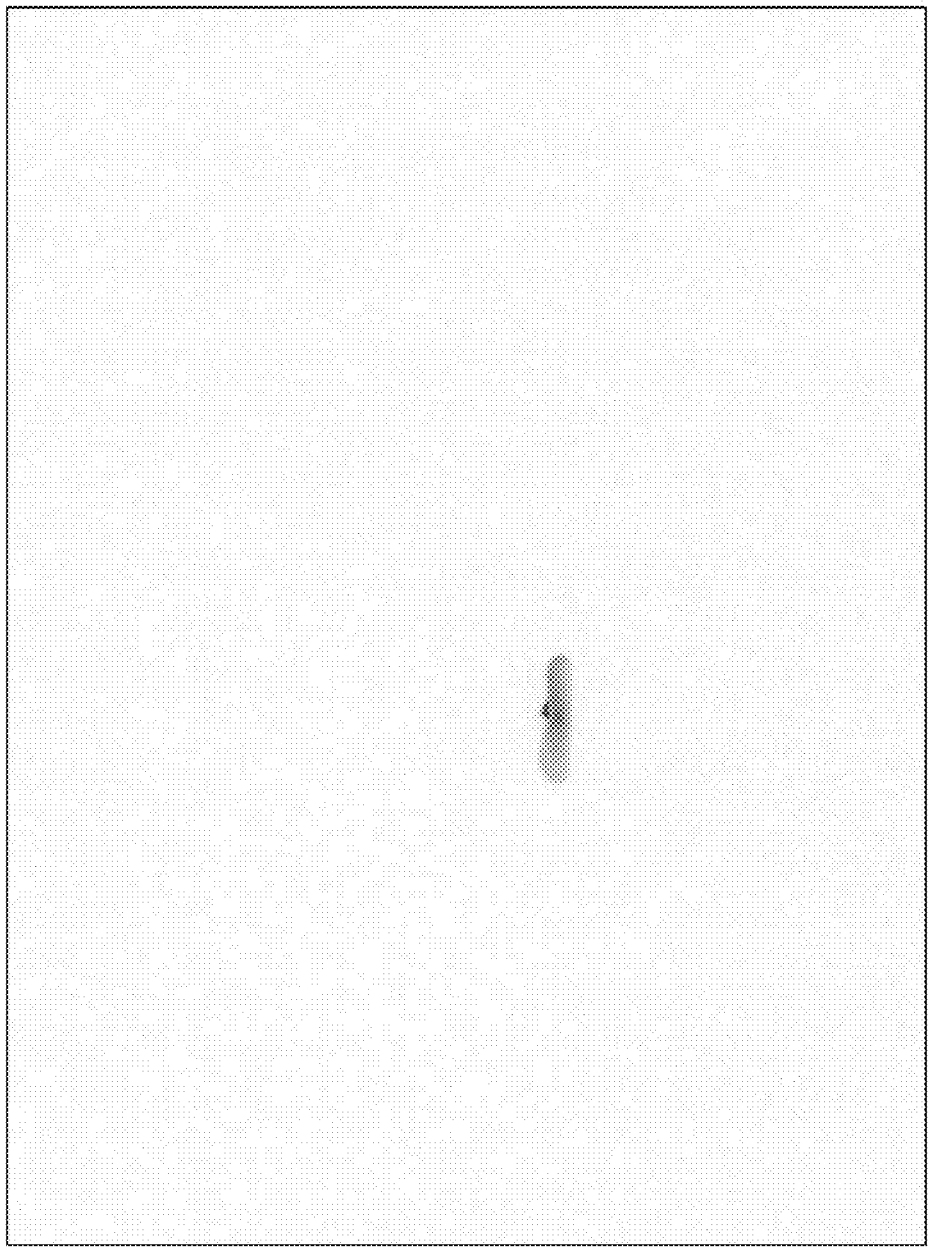
Figure 26:
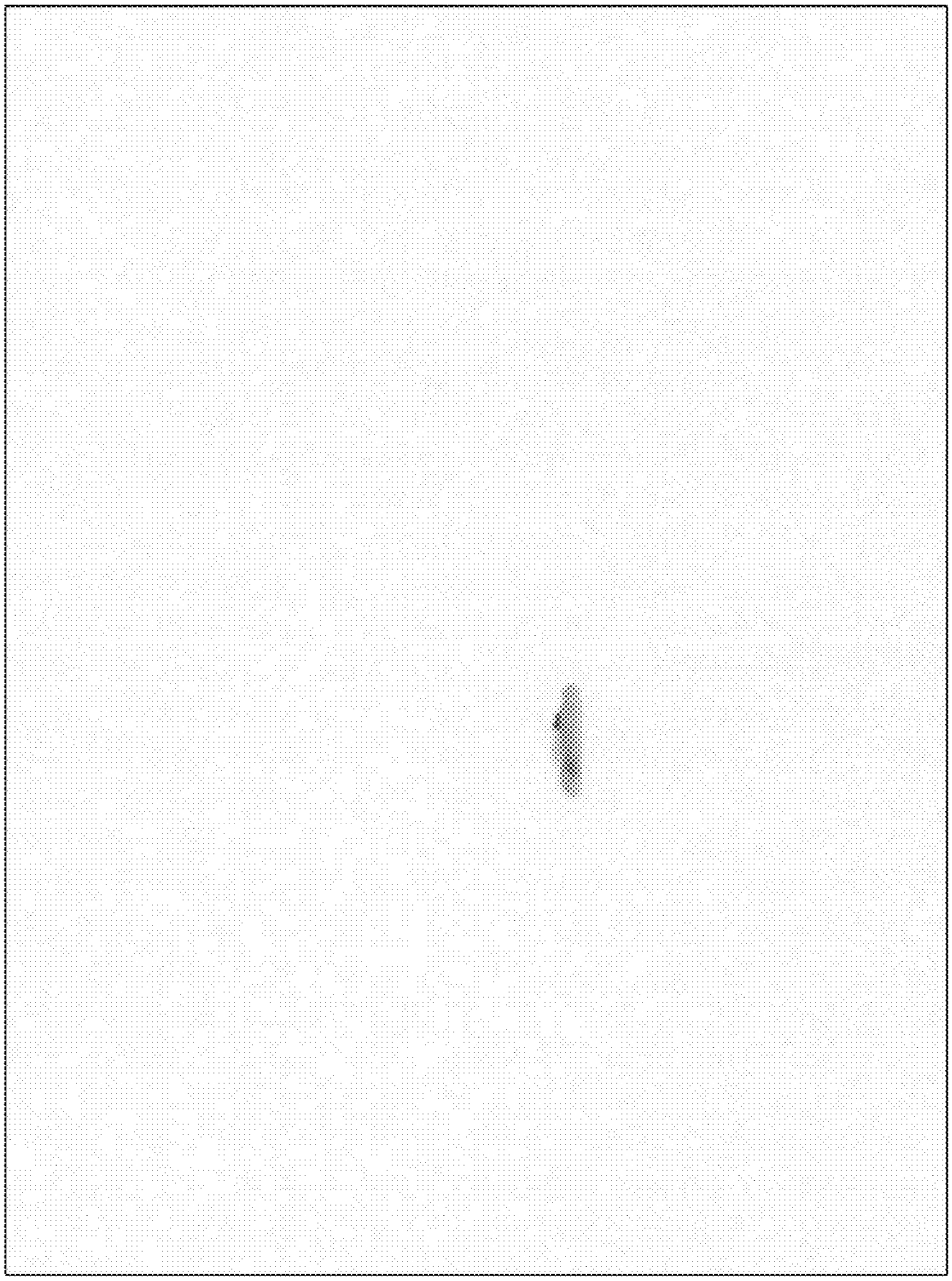
Figure 27:
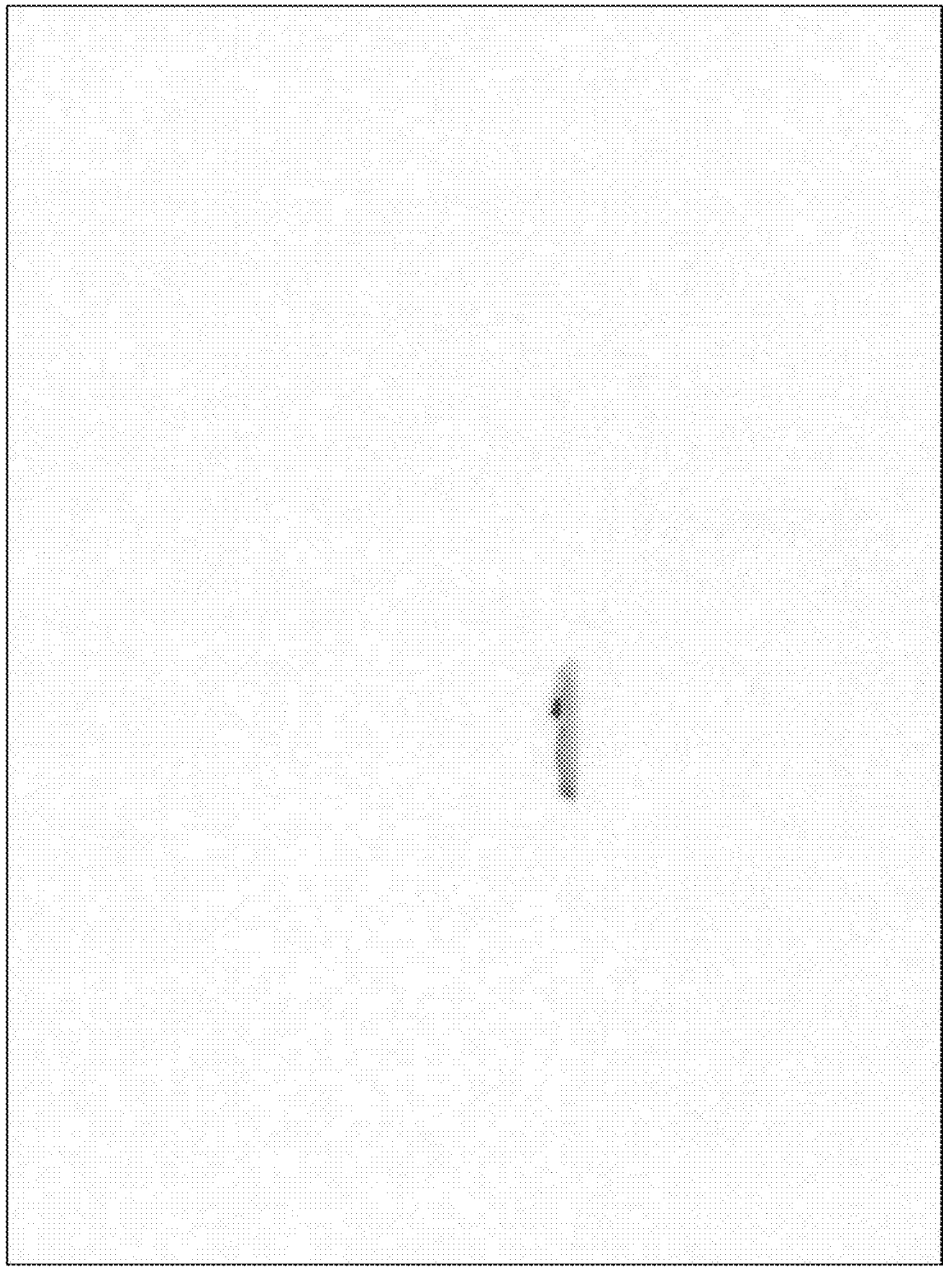
Figure 28:
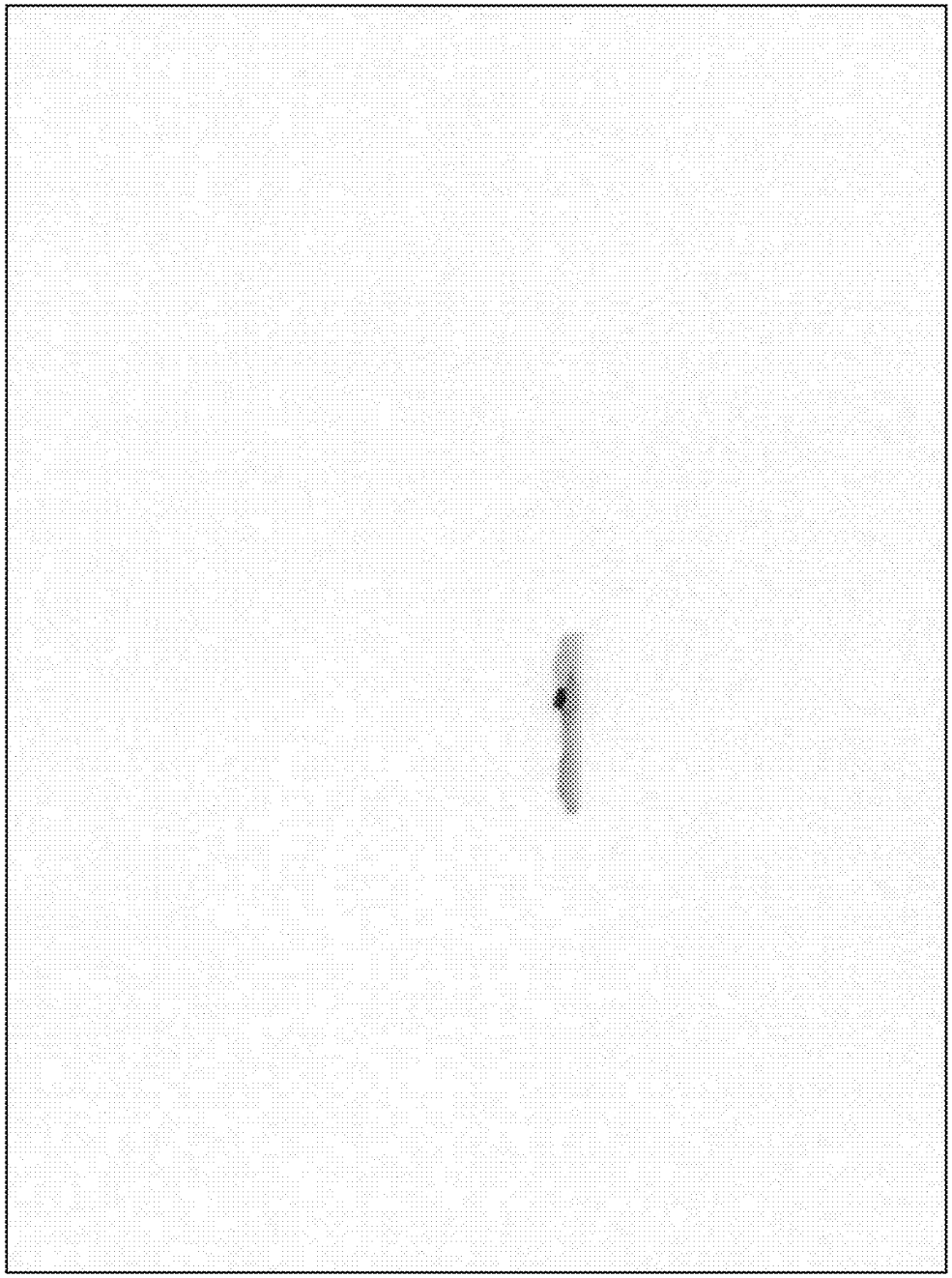
Figure 29:
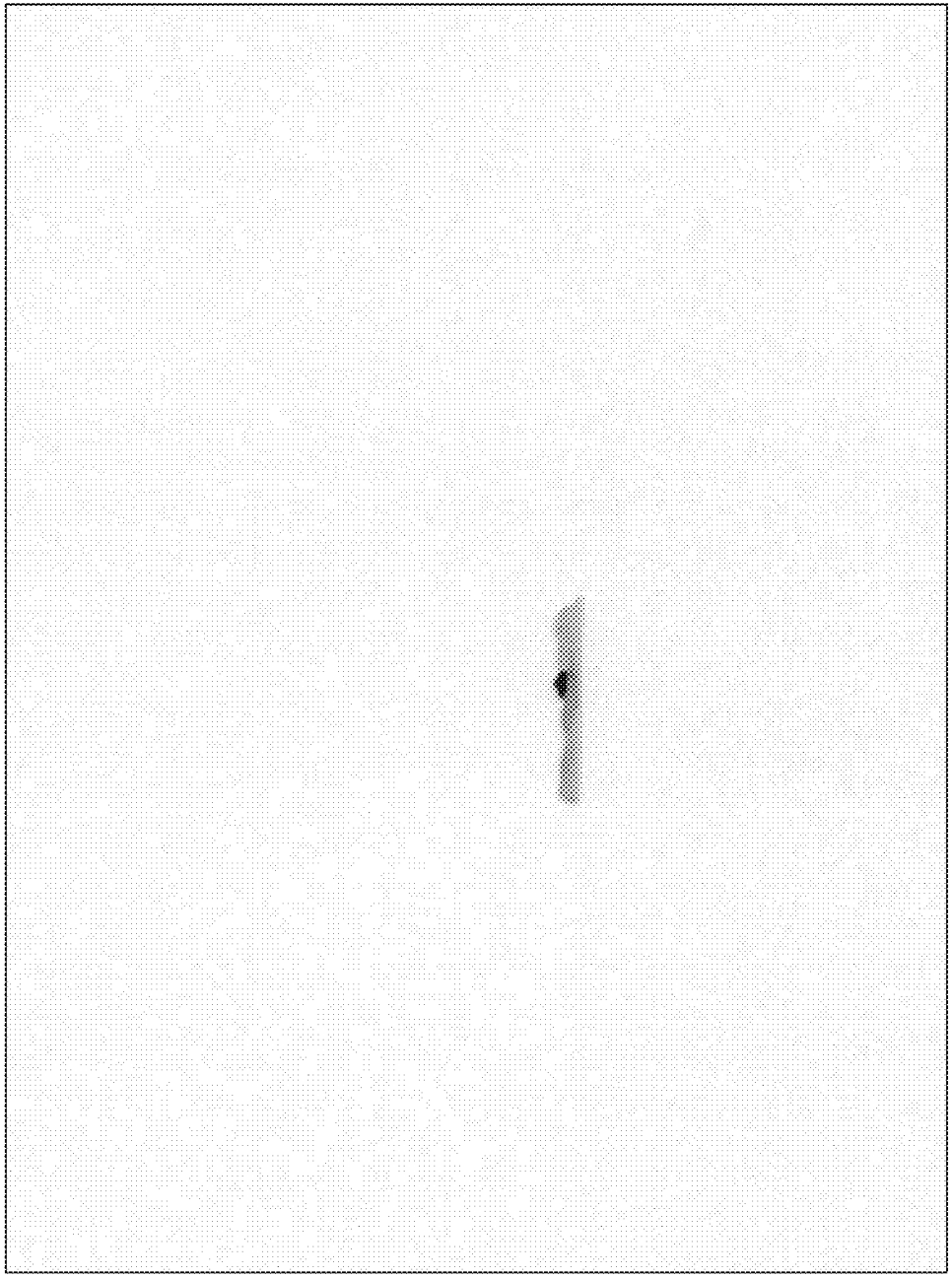
Figure 30:
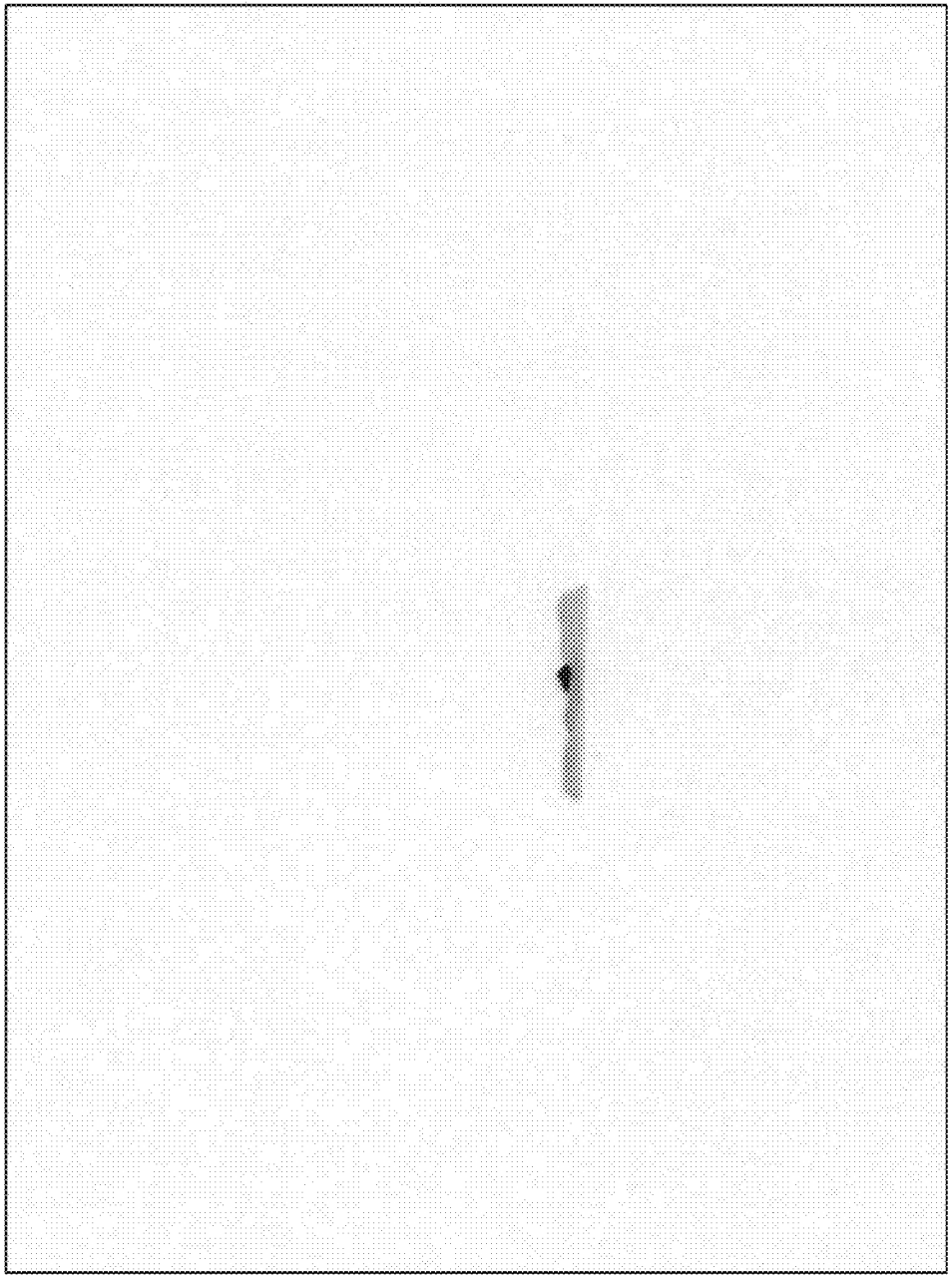
Figure 31:
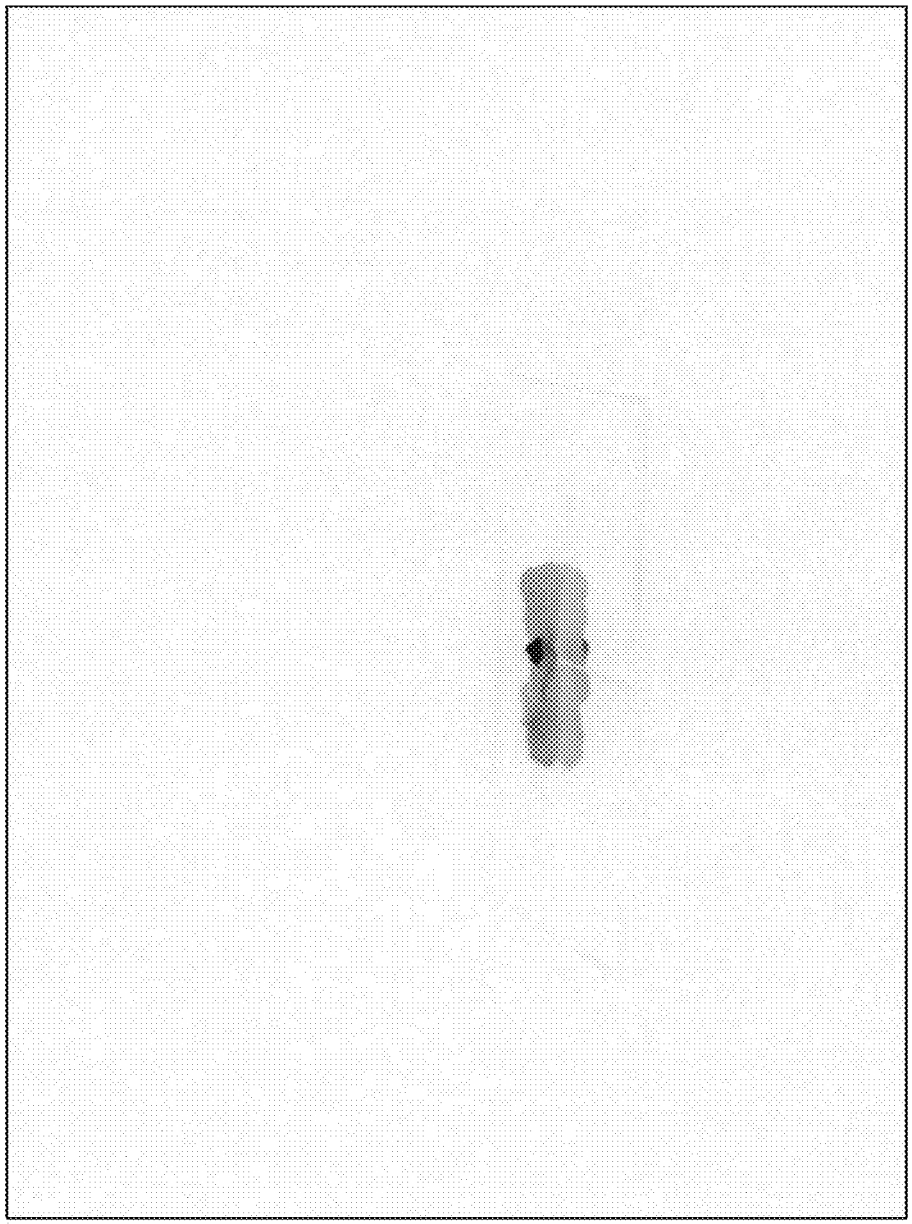
Figure 32:
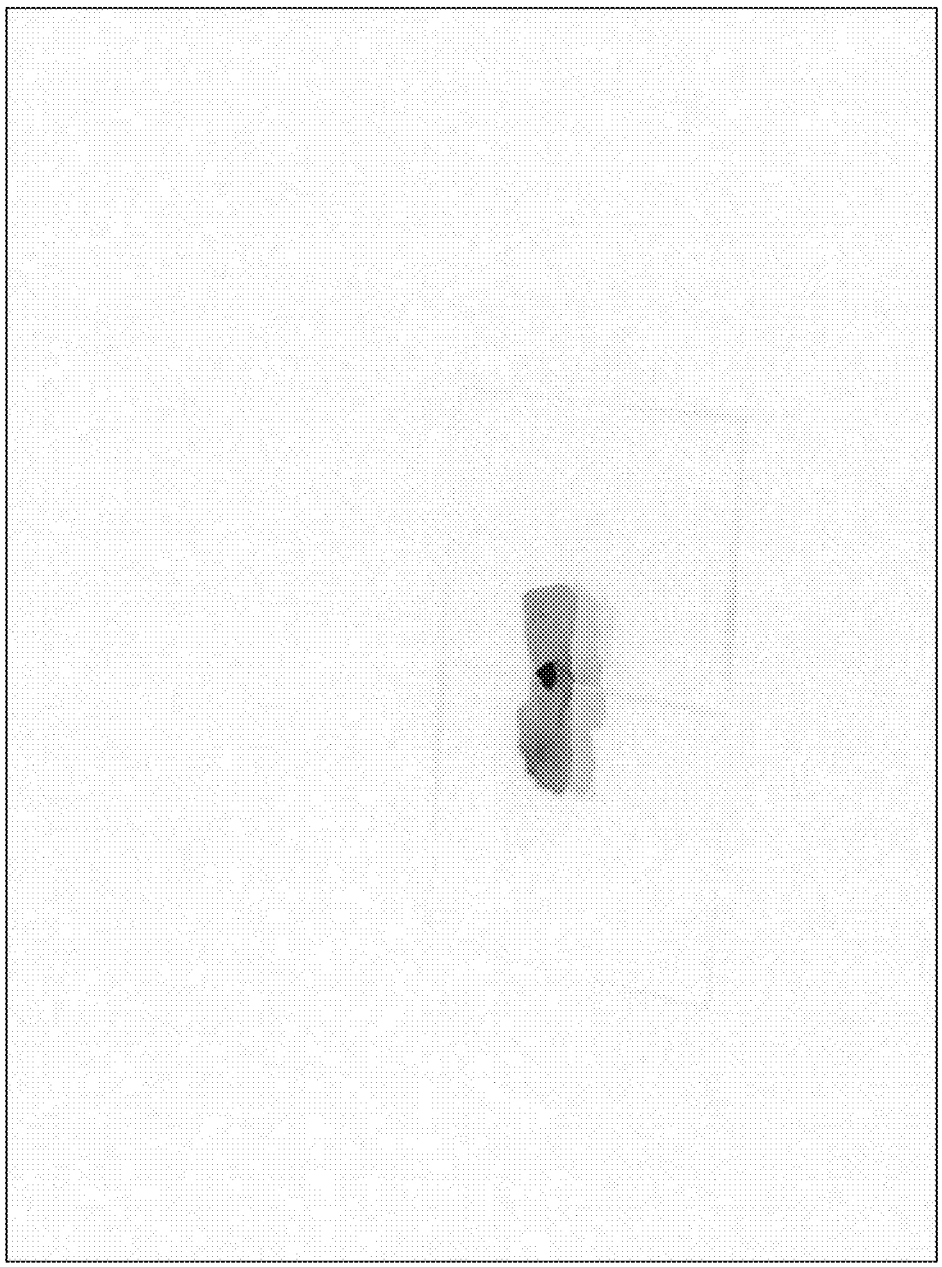
Figure 33:
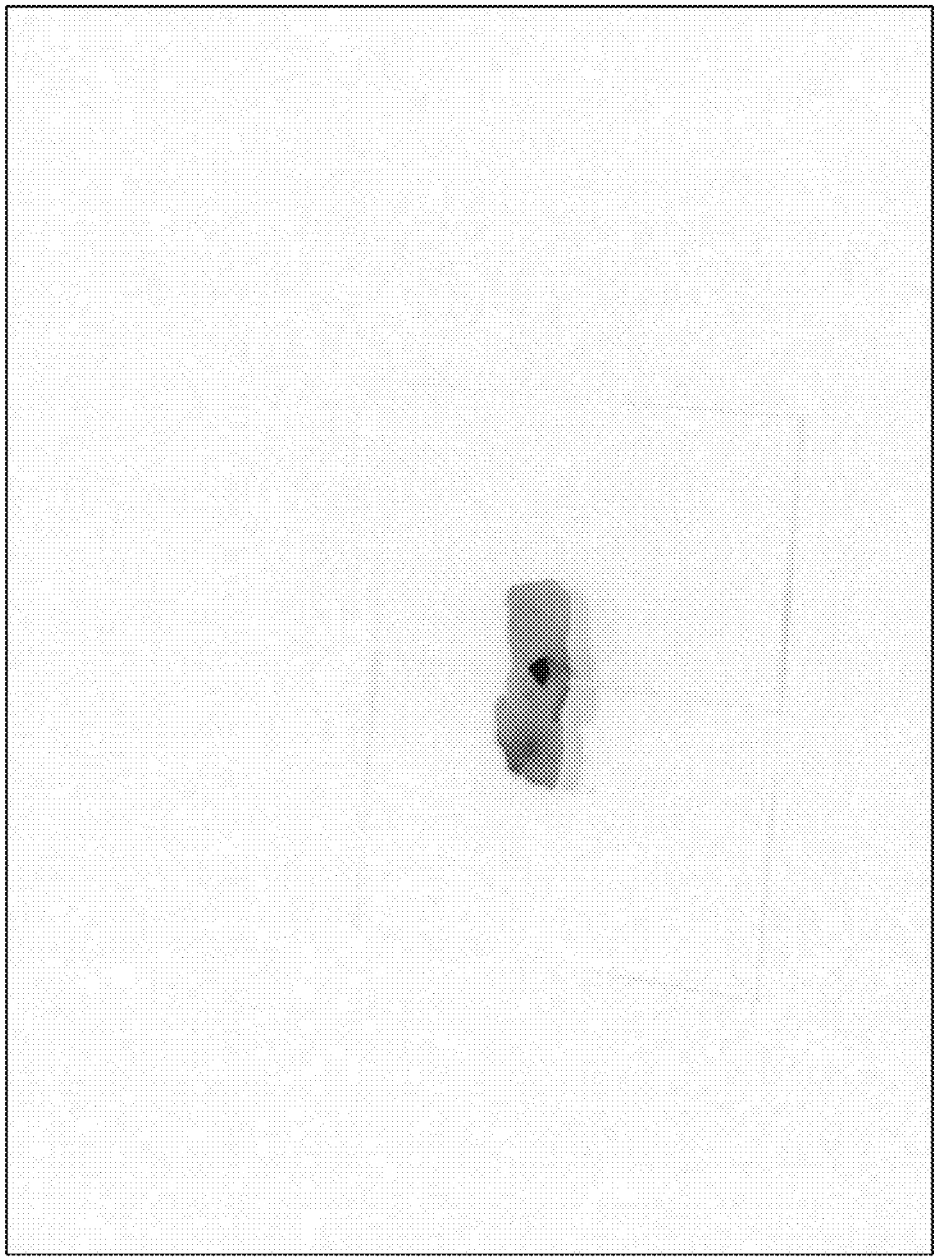
Figure 34:
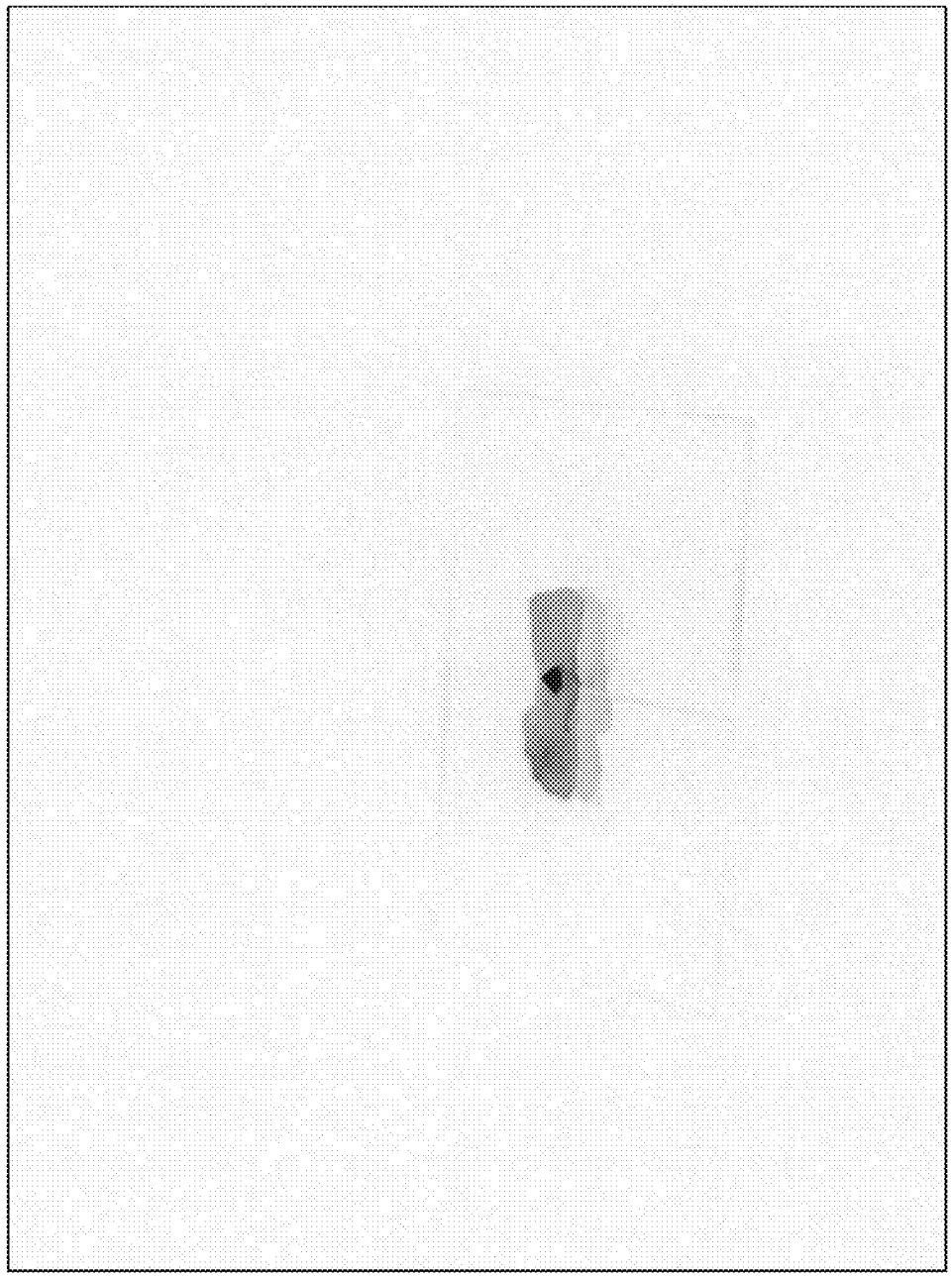
Figure 35:
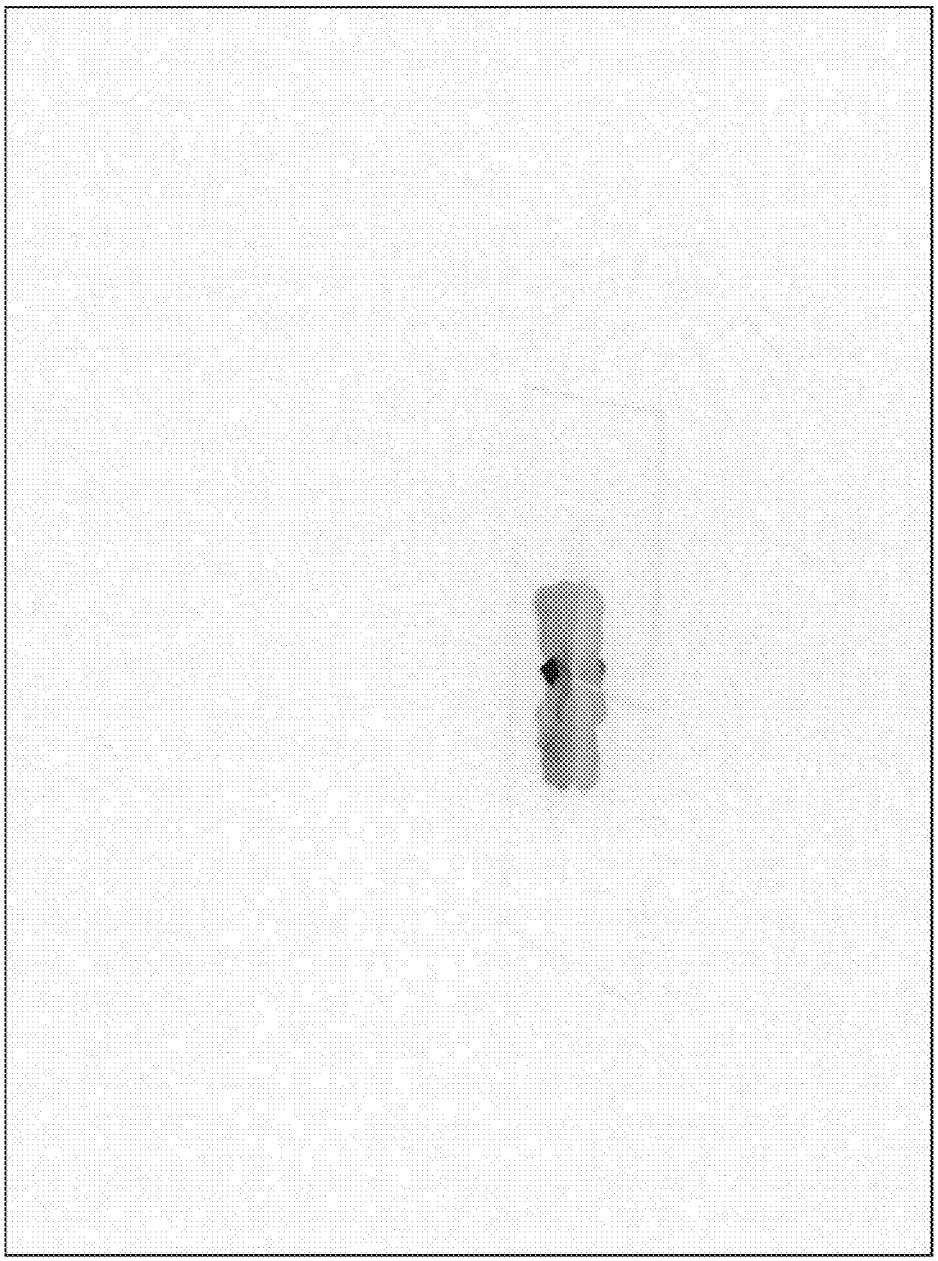
Figure 36:
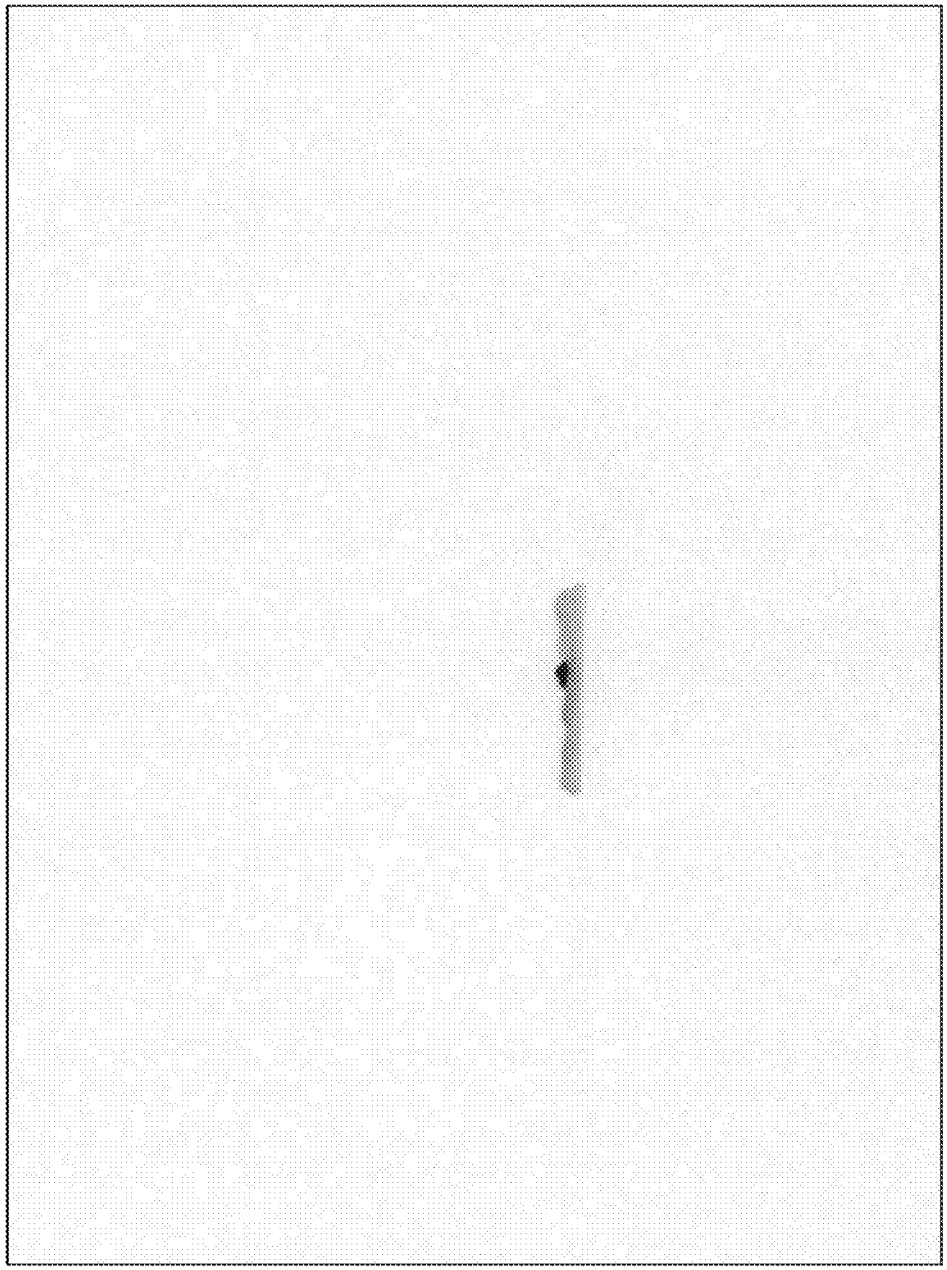
Figure 37:
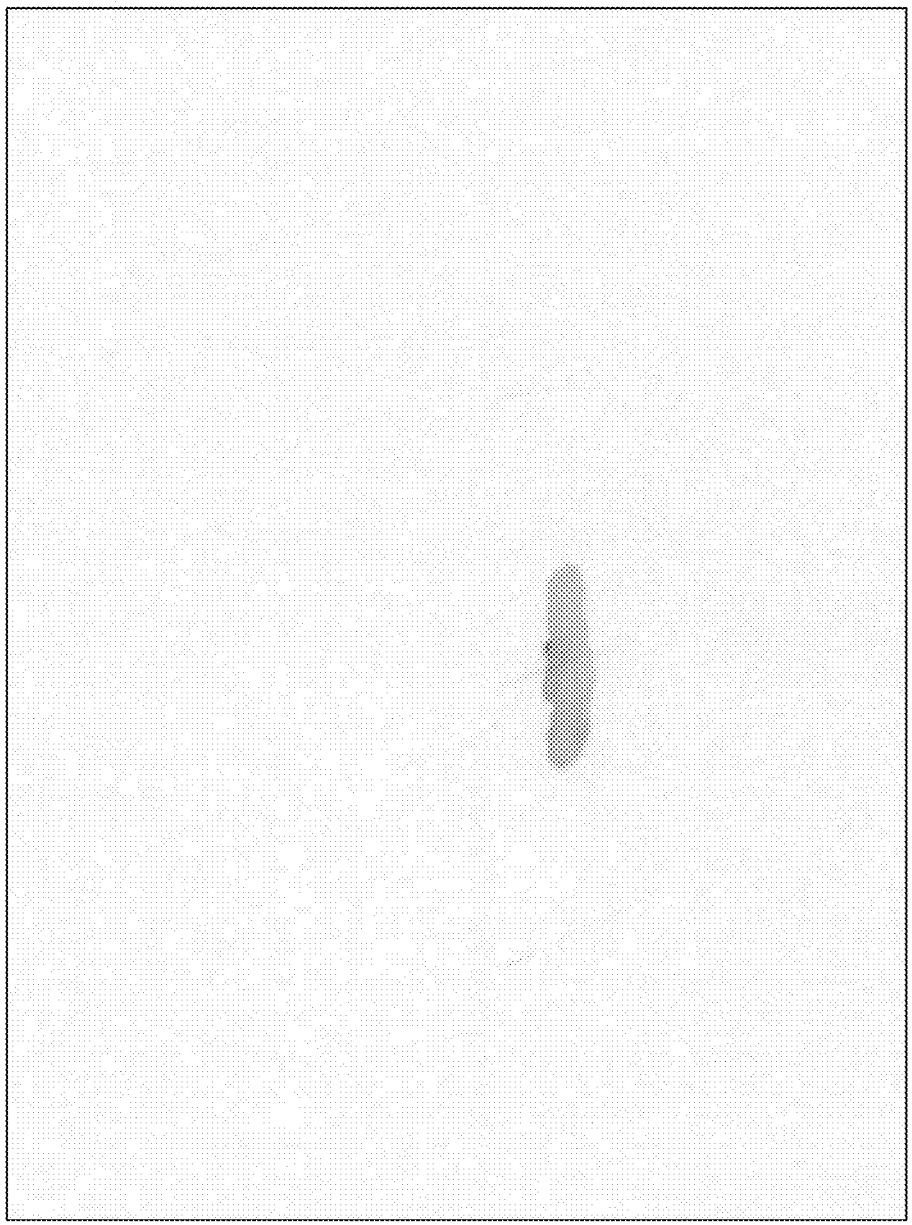
Figure 38:
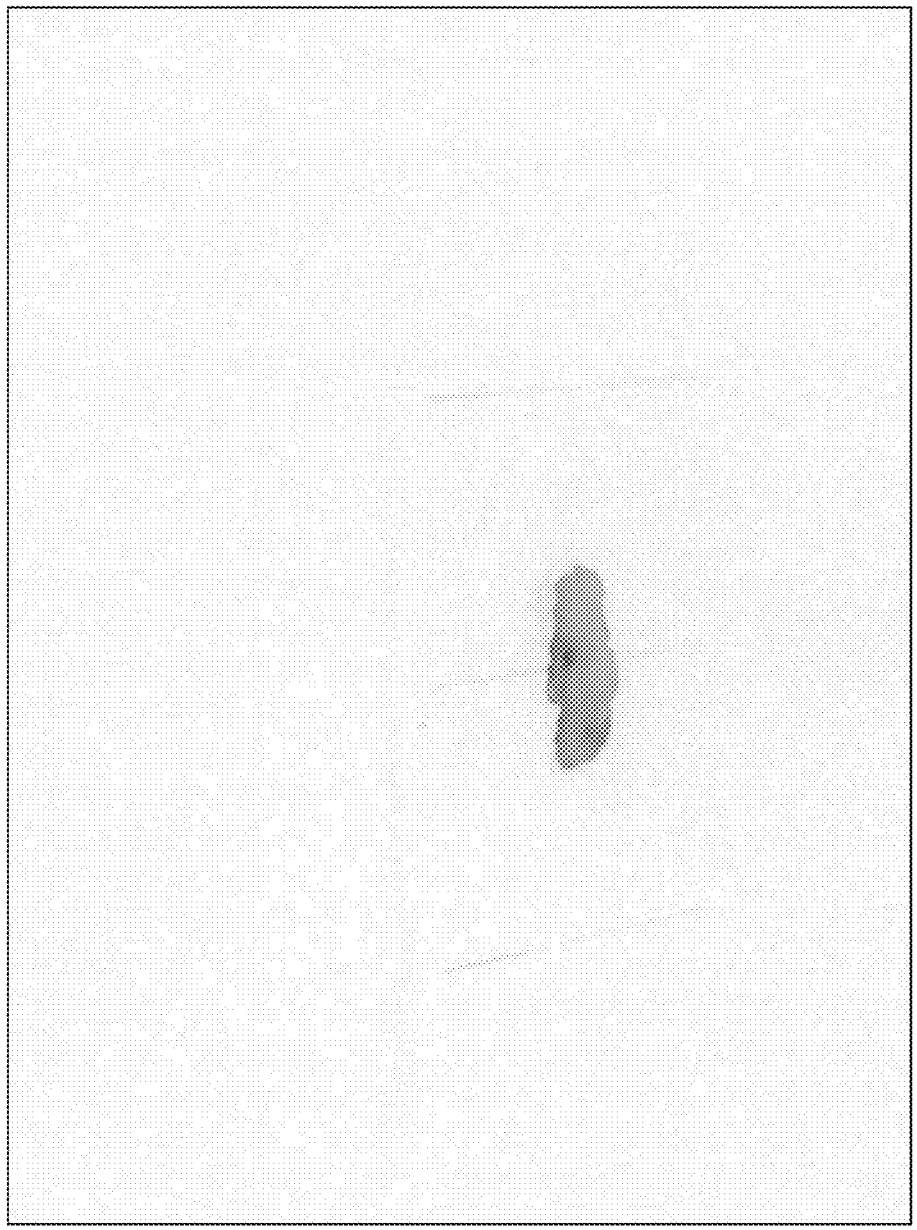
Figure 39:
Figure 40:
Figure 41:
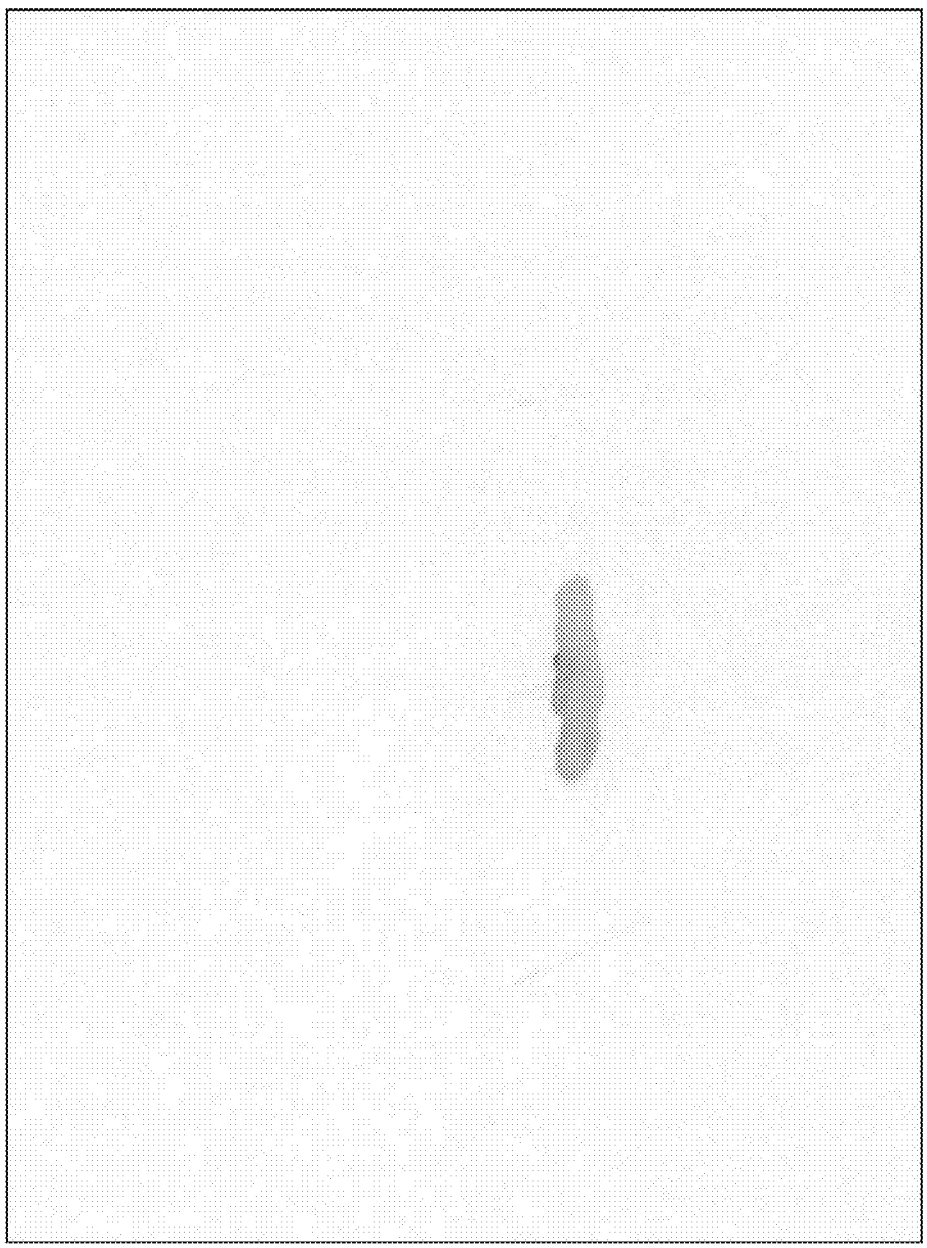

In FIGS. 13A and 13B, an interactive animation allows the user to scroll through the 3D result and take a specific view for detail inspection. FIG. 13A shows an example of a user scrolling in a rolling mode. That is, a user can apply touch gestures to scroll through different azimuth viewpoint angles around a single elevation. FIG. 13B shows an example of a user scrolling in a pitching/tilting mode. That is, a user can apply touch gestures to scroll through different elevation viewpoint angles along a single azimuth.

Furthermore, an augmented reality display interface will allow the user to review 3D views by rolling and tilting the tablet display in which a gyroscope package senses the motion and provides the information to interact with the image output.

A 3D reconstruction algorithm can offer full-rotation 3D model for an augmented reality application. In the reconstruction algorithm one can apply volume carving to form spatial volume, together with feature recognition techniques to locate common features. A projection method known as "silhouette projection" takes an image into a virtual volume by carving away the voxels outside the silhouette projection at each view angle. Overall geometry of an object can then be derived. By matching common features, an object can be verified and incorporated into the model. After the model is created, an intensity scalar related to the adjusted fluorescence color map of each view is retrieved for 3D rendering. Coordinates, features, and scalars defined in the volume reconstruction process are used to match 2D and 3D results in rendering the signal distribution. Tissue mimicking phantoms and tissue constructs are accounted for in algorithm validation.

As current tablet displays commonly have a refresh rate of ≥60 Hz and a response time of <8 ms, the input lagging of an augmented reality 3D model is determined by the application algorithm. An input lag can be measured and expected to achieve ≤100 ms lagging for a typical 3D model so that user will not experience serious human detectable latency while viewing a model interactively.

FIGS. 14 through 40 illustrate overlaid full-color and fluorescence images of an object at different angles in accordance with an embodiment. Flipping through the figures rapidly shows a short animation. The first 17 images complete a 360° circuit around the sample at 22.5° increments, ending at the same azimuth angle as the beginning image. The next 11 images show the sample from higher and lower elevations (i.e., higher and lower tilts) at a constant azimuth angle.

The animation can be automatically played or can be interactively controlled. For example, a surgeon can stop the animation at a selected frame, zoom in, or tilt up and down to see more of the sample.

In a surgical workflow, a surgeon who operates a surgery only touches tools that are sterilized. In some surgical procedures, a technologist or other staff member assists a surgeon by helping to manipulate information presented on a display of any instrument. However, actions taken by the staff may not accurately or effectively accord with the verbal commands and requests from a surgeon. As a result, there can be a benefit to enabling surgeons to work with a display or instrument directly. Touching of instruments such as a computer, keyboards, display panels, or a cabinet imager may break the sterilization, though, and create contamination problems. The use of a sterile touch pen to operate a display or interface on a screen can therefore assist in maintaining a sterile environment in an operating room.

Figure 42:
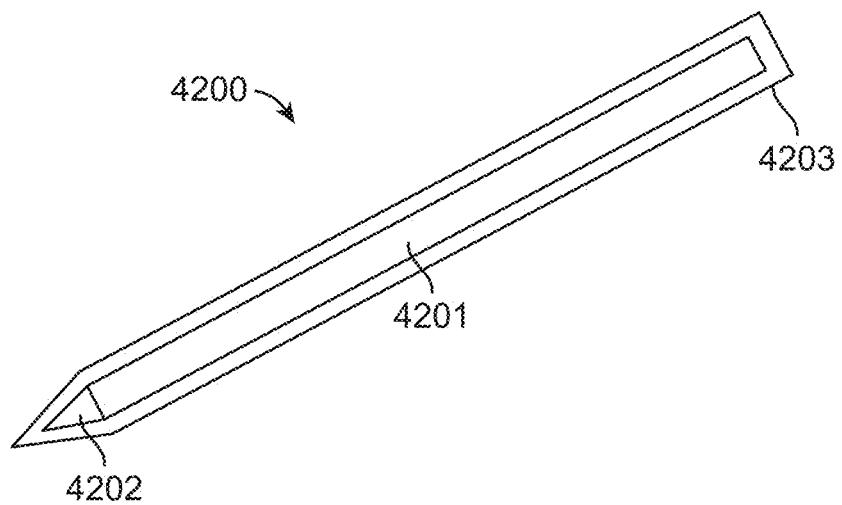
FIG. 42 is an illustration of a touch pen in accordance with an embodiment.

FIG. 42 illustrates one embodiment as a descriptive example. Shown is a touch pen 4200 comprising a pen body 4201 and a pen tip 4202. The touch pen can also comprise a pen cover 4203 that encloses the pen body 4201 and the pen tip 4202.

The pen body 4201 can be made of disposable and pre-sterilized material intended for one-time or limited-time use. The pen body 4201 can be or made of sterilizable material intended for repeated use with sterilization occurring prior to each use. In some embodiments, one or both of the pen body 4201 and the pen tip 4202 comprise a metal. In some embodiments, the metal is stainless steel. In some embodiments, the pen tip 4202 is detachable from the pen body 4201. The pen tip 4202 can be made of disposable and pre-sterilized material intended for one-time or limited-time use. The touch pen can be enclosed in a pen cover 4203 that is made of disposable and pre-sterilized material intended for one-time or limited-time use. In some embodiments, the pen body 4201 and pen tip 4202 are not sterile, but the pen cover 4203 is sterile. In some embodiments, the touch pen can dispense ink. In some embodiments, the touch pen does not dispense ink.

An embodiment can use a high-performance monochrome imaging camera with a CCD sensor. With advances in CMOS imaging sensors, CMOS sensors may become the norm in fluorescence applications.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. An apparatus for imaging a biological sample with fluorescence, the apparatus comprising:
    a rotatable imaging stage adapted for supporting at least a portion of a biological sample within an imaging volume;
    a first camera;
    a monochromatic second camera; and
    a switchable mounting system configured to alternatingly position the first camera and the second camera to receive light reflecting or emitting from the biological sample.

2. The apparatus of claim 1 further comprising:
    a fluorescence excitation light source configured to illuminate the imaging volume.

3. The apparatus of claim 1 further comprising:
    a preview third camera having an optical system focused on the imaging volume.

4. The apparatus of claim 1 further comprising:
    a transparent window having a plurality of equally spaced marks at predetermined intervals, the transparent window attached to the imaging stage.

5. The apparatus of claim 4 further comprising:
    a computer processor operatively connected with a machine-readable non-transitory medium embodying information indicative of instructions for causing the computer processor to perform operations comprising:
        taking reflected light images of a biological sample on the stage using the first camera, the reflected light images including the equally spaced marks;
        collecting fluorescence images of the biological sample using the second camera;
        detecting the equally spaced marks in the reflected light images or the fluorescence images; and
        extrapolating the equally spaced marks in order to determine a three-dimensional position of a portion of the biological sample.

6. An apparatus for imaging a biological sample with fluorescence, the apparatus comprising:
    a rotatable imaging stage adapted for supporting at least a portion of a biological sample within an imaging volume;

a transparent window having a plurality of equally spaced marks at predetermined intervals, the transparent window attached to the imaging stage;
a first camera;
a monochromatic second camera; and
a partially reflective mirror, the mirror configured to reflect a portion of an image of the at least a portion of the biological sample to one of the cameras, and the mirror configured to transmit a portion of the image to the other of the cameras.

7. The apparatus of claim 6 further comprising:
a fluorescence excitation light source configured to illuminate the imaging volume.

8. The apparatus of claim 6 further comprising:
a preview third camera having an optical system focused on the imaging volume.

9. The apparatus of claim 6 further comprising:
a computer processor operatively connected with a machine-readable non-transitory medium embodying information indicative of instructions for causing the computer processor to perform operations comprising:
taking reflected light images of a biological sample on the stage using the first camera, the reflected light images including the equally spaced marks;
collecting fluorescence images of the biological sample using the second camera;
detecting the equally spaced marks in the reflected light images or the fluorescence images; and
extrapolating the equally spaced marks in order to determine a three-dimensional position of a portion of the biological sample.

10. An apparatus for imaging a biological sample with fluorescence, the apparatus comprising:
a rotatable imaging stage adapted for supporting at least a portion of a biological sample within an imaging volume;
a first camera;
a monochromatic second camera;
a flip mirror; and
an optical system configured to present an image of the at least a portion of the biological sample to the flip mirror, the flip mirror having a first configuration for reflecting the image to the first camera and a second configuration for reflecting the image to the second camera.

11. The apparatus of claim 10 further comprising:
a fluorescence excitation light source configured to illuminate the imaging volume.

12. The apparatus of claim 10 further comprising:
a preview third camera having an optical system focused on the imaging volume.

13. The apparatus of claim 10 further comprising:
a transparent window having a plurality of equally spaced marks at predetermined intervals, the transparent window attached to the imaging stage.

14. The apparatus of claim 13 further comprising:
a computer processor operatively connected with a machine-readable non-transitory medium embodying information indicative of instructions for causing the computer processor to perform operations comprising:
taking reflected light images of a biological sample on the stage using the first camera, the reflected light images including the equally spaced marks;
collecting fluorescence images of the biological sample using the second camera;
detecting the equally spaced marks in the reflected light images or the fluorescence images; and
extrapolating the equally spaced marks in order to determine a three-dimensional position of a portion of the biological sample.

15. A method of correcting an image for divergence of fluorescence excitation light, the method comprising:
illuminating a biological sample on a stage with a fluorescence excitation light source;
taking a first fluorescence image of the biological sample using a camera;
rotating the stage from a first angle to a second angle;
collecting a second fluorescence image of the biological sample using the camera;
determining from the fluorescence images a three-dimensional position of a portion of the biological sample;
ascertaining a divergence of the fluorescence excitation light;
acquiring a pixel reading of one of the images; and
applying a correction to the pixel reading based on the three-dimensional position and the divergence.

16. The method of claim 15 wherein the correction is based on a predetermined, calculated divergence of the fluorescence excitation light.

* * * * *